(12) United States Patent
Avnur et al.

(10) Patent No.: US 6,201,109 B1
(45) Date of Patent: Mar. 13, 2001

(54) ASSAY FOR BONE ALKALINE PHOSPHATASE

(75) Inventors: Zafrira Avnur, Cupertino; Suzanna S. Pedersen, Sunnyvale; Mary Jane Cerelli, Burlingame; Thomas D. Kempe, Sunnyvale, all of CA (US)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/003,894

(22) Filed: Jan. 13, 1993

(51) Int. Cl.$^7$ .................................................. A61K 39/395
(52) U.S. Cl. ...................... 530/388.26; 435/7.4; 435/7.72
(58) Field of Search ......................... 530/388.26; 435/7.4, 435/7.72

(56) References Cited

U.S. PATENT DOCUMENTS

| Re. 32,696 | 6/1988 | Schuurs et al. | 435/7 |
|---|---|---|---|
| 4,244,940 | 1/1981 | Jeong et al. | 424/1 |
| 4,271,140 | 6/1981 | Bunting | 424/1 |
| 4,474,892 | 10/1984 | Murad et al. | 436/513 |
| 4,659,678 | 4/1987 | Forrest et al. | 436/512 |
| 4,935,339 | 6/1990 | Zahradnik | 435/5 |
| 5,087,573 | 2/1992 | Anderson et al. | 435/240 |
| 5,173,406 | * 12/1992 | Hosoda et al. | 435/7.72 |
| 5,248,592 | * 9/1993 | Tischer et al. | 435/7.4 |

FOREIGN PATENT DOCUMENTS

| 381 450 A2 | 8/1990 | (EP) . |
| 2074727 | 11/1981 | (GB) . |
| 2190490 | 11/1987 | (GB) . |

OTHER PUBLICATIONS

Wada, et al., *Cancer Research*, vol. 48 (Apr. 15, 1988), pp. 2273–2279, "Monoclonal Antibodies That Detect Different Antigenic Determinants of the Same Human Osteosarcoma-associated Antigen".
Singh, et al., *Experimental Cell Research*, vol.95: pp. 347–358 (1975).
Bailyes, et al., *Biochemistry J.*, vol. 244: pp. 725–733 (1987).
Mulivor, et al., *Journal Lab. Clin. Med.*, vol. 105(3): pp. 342–347 (1985).
Hill, et al., *Clinica Chimica Acta*, vol. 186: pp. 315–320 (1989).
Hill, et al., *Journal of Bone and Mineral Research*, vol. 6: Suppl 1, S244 (1991).
Masuhara, et al., *International Orthopaedics*, vol. 15: pp. 61–64 (1991).
Seabrook, et al., *Clinica Chimica Acta*, vol. 172: pp. 261–266 (1988).
Nagoya, et al., *Jpn. Journal Cancer Research*, vol. 82: pp. 862–870 (1991).
Lawson, et al., *Clinical Chemistry*, vol. 31:(3), pp. 381–385 (1985).

* cited by examiner

*Primary Examiner*—Scott W Houtteman

(57) ABSTRACT

This invention relates to novel monoclonal antibodies XI-4G6, XII-10E3 and XII-3B2, which are capable of recognizing bone alkaline phosphatase and not liver alkaline phosphatase. Methods and kits for using these antibodies in the determination of bone alkaline phosphatase are also described.

16 Claims, 5 Drawing Sheets

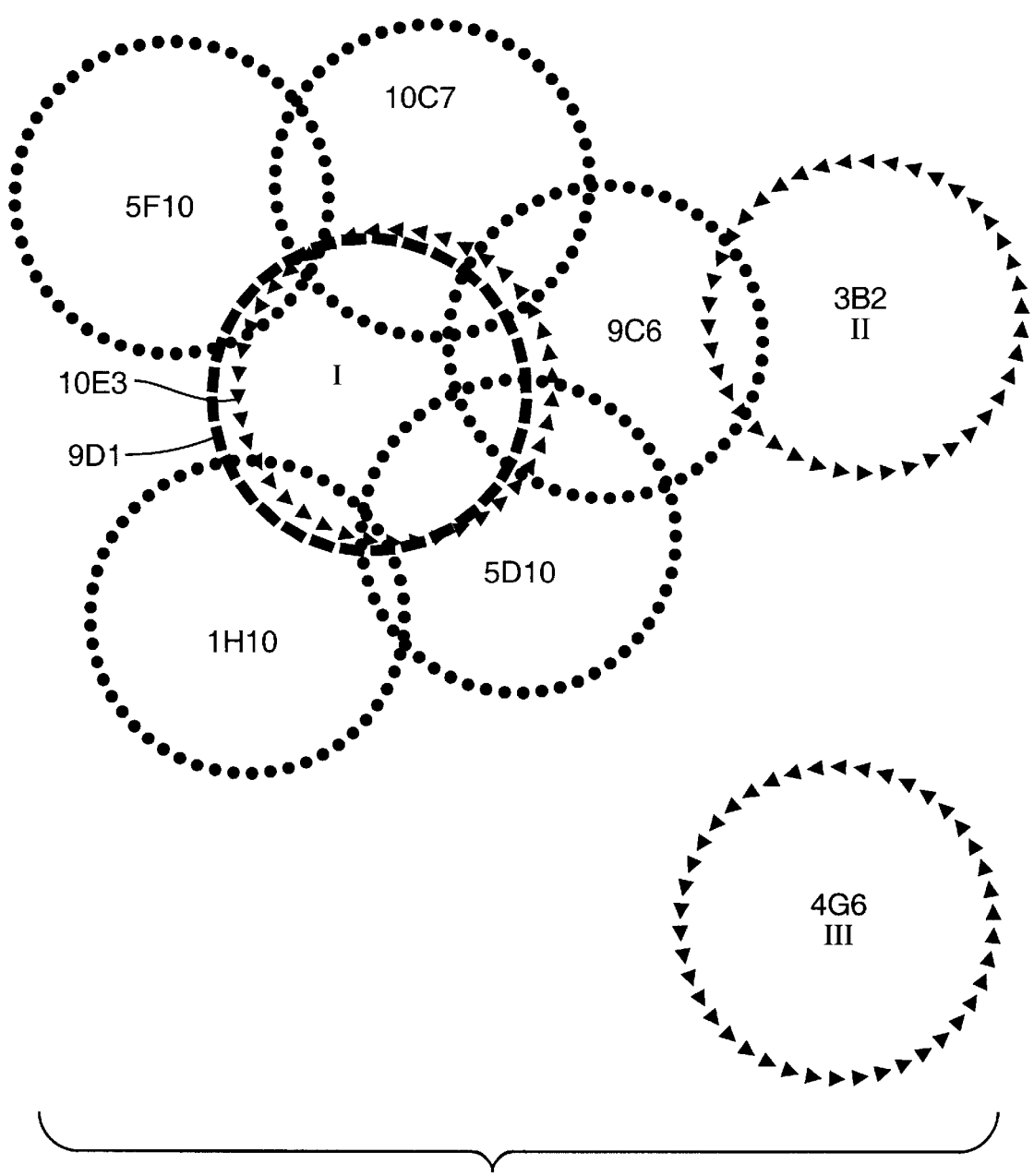
FIG._1

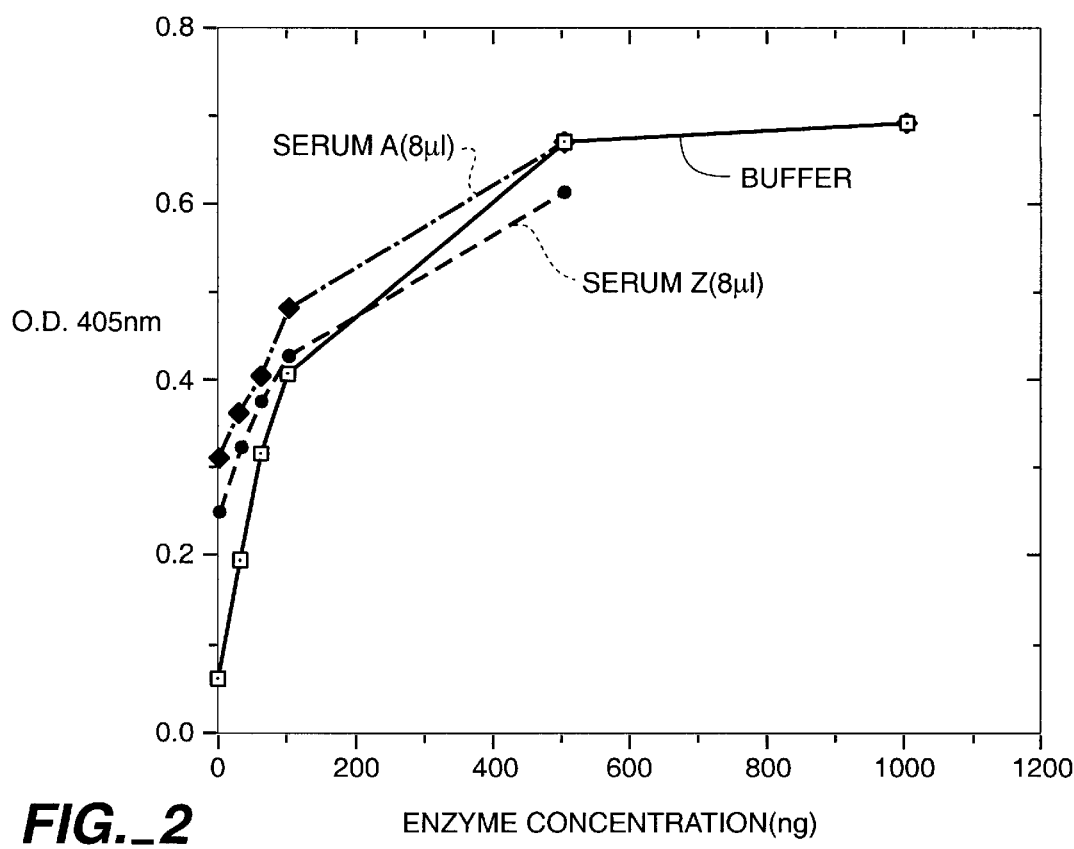
FIG._2
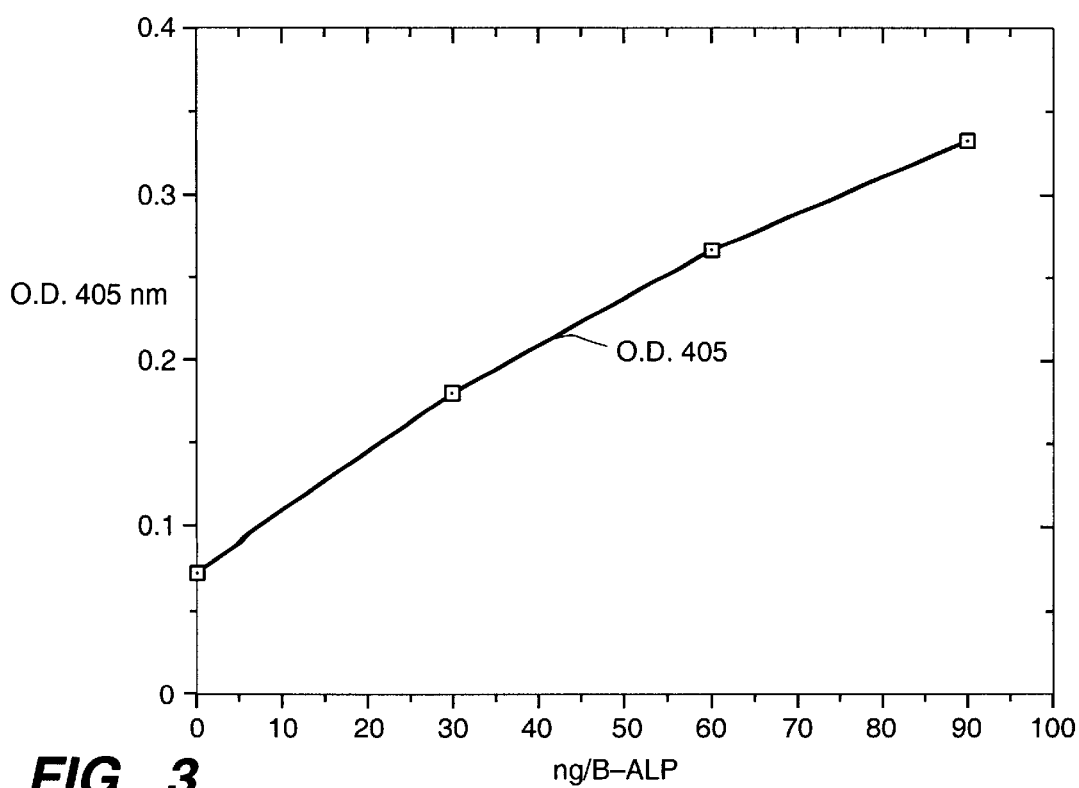
FIG._3

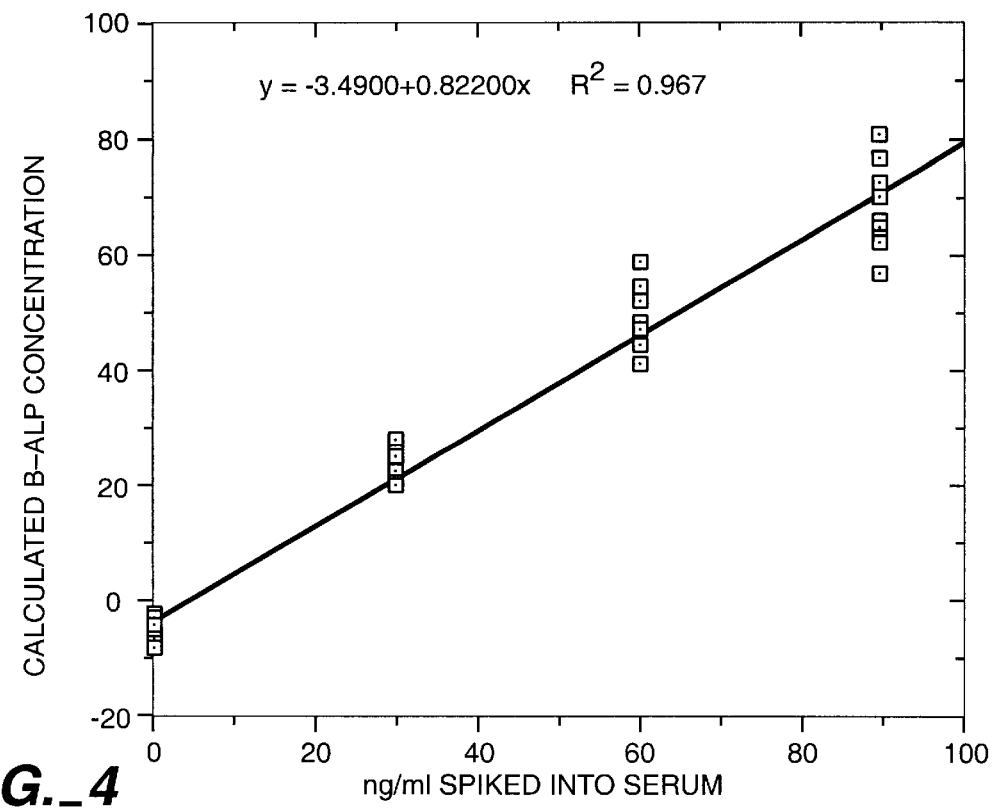
FIG._4
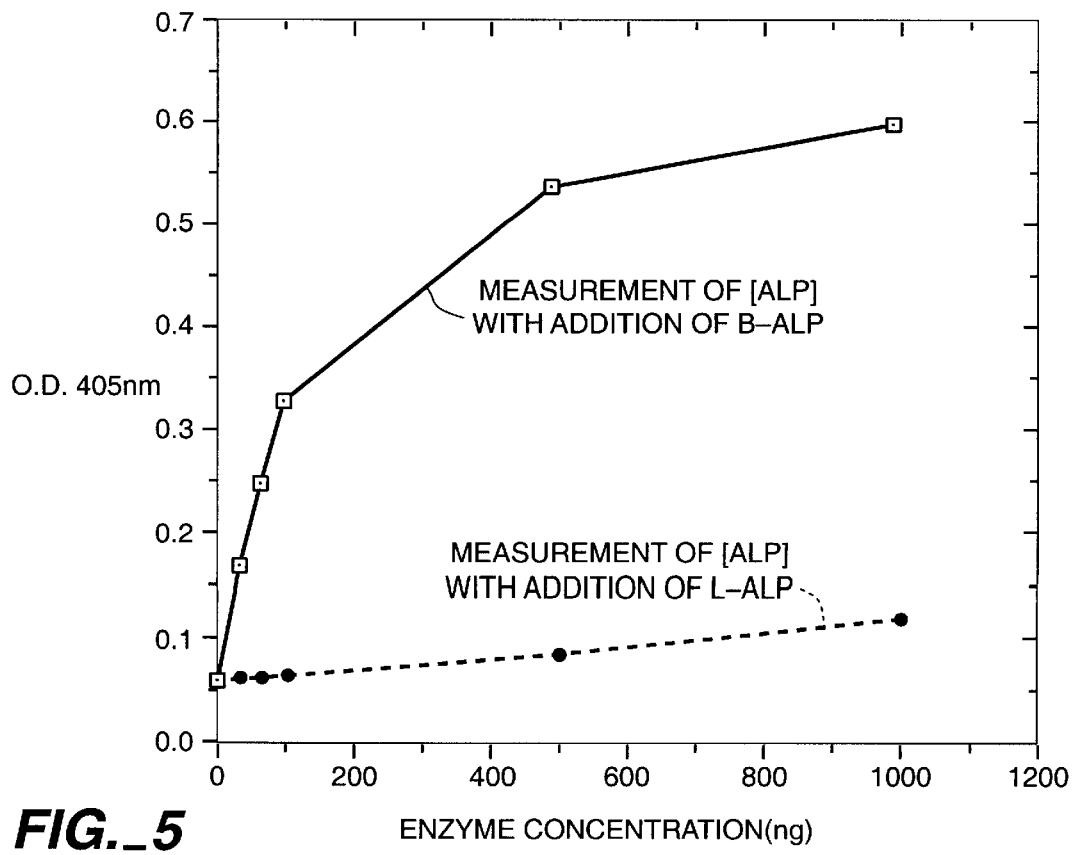
FIG._5

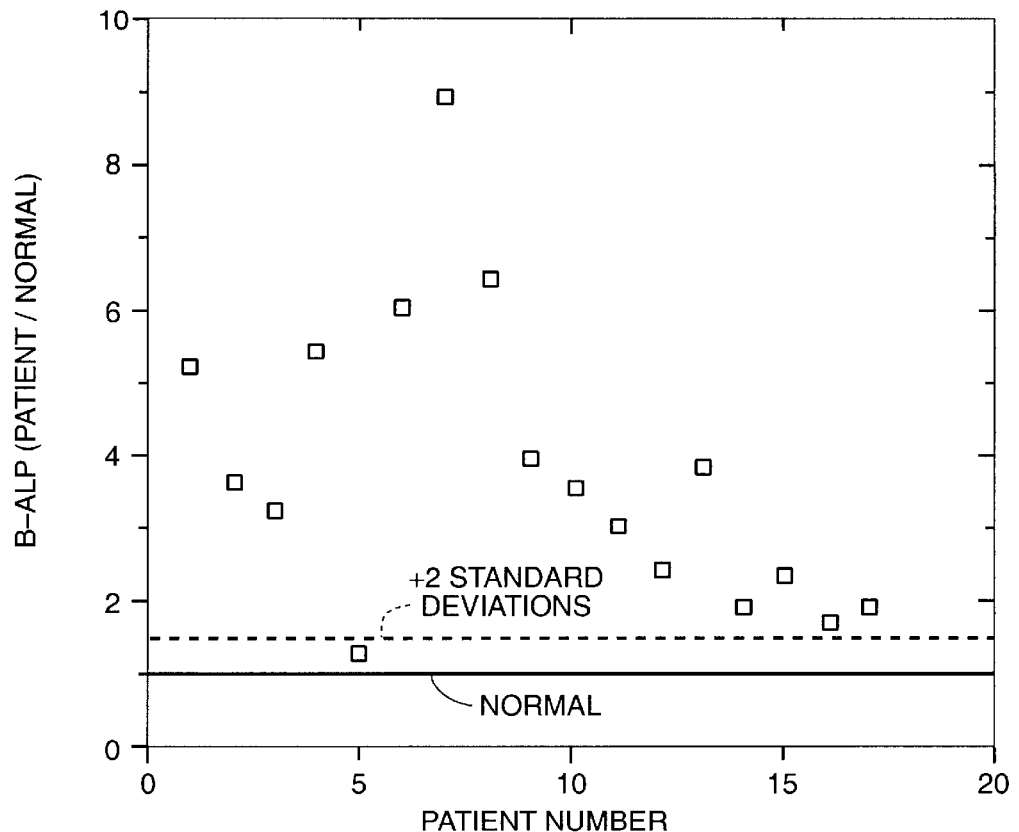
FIG._6
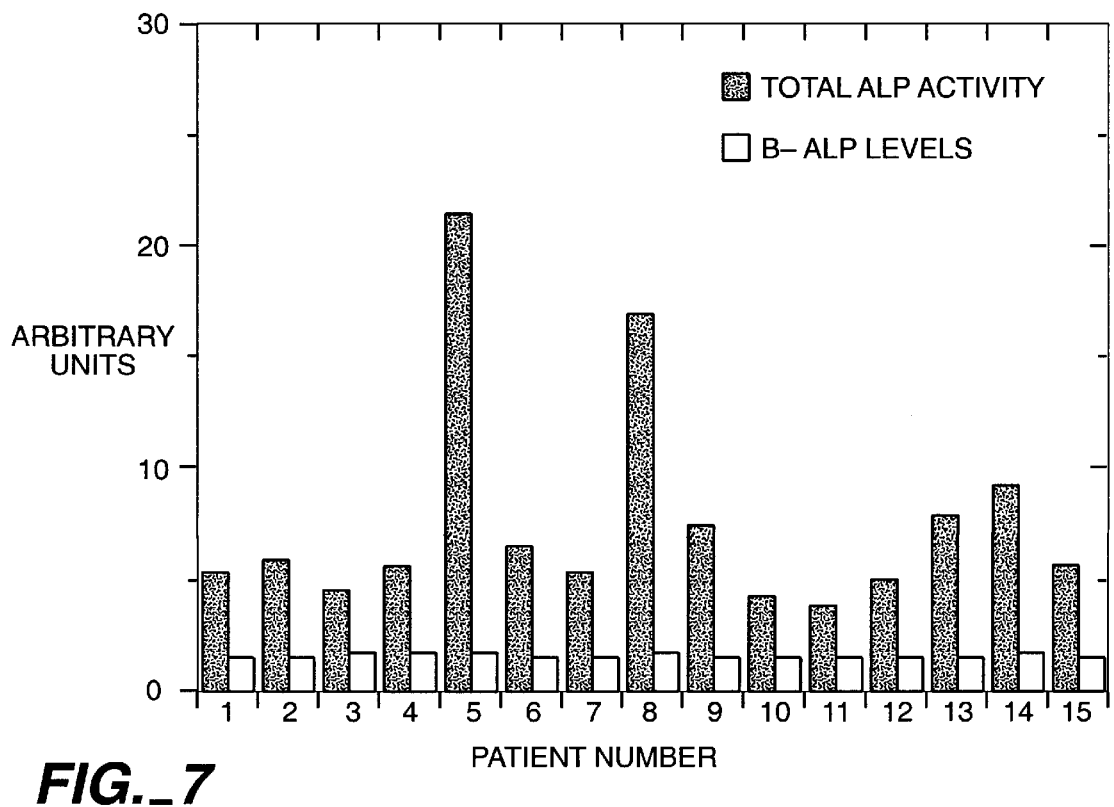
FIG._7

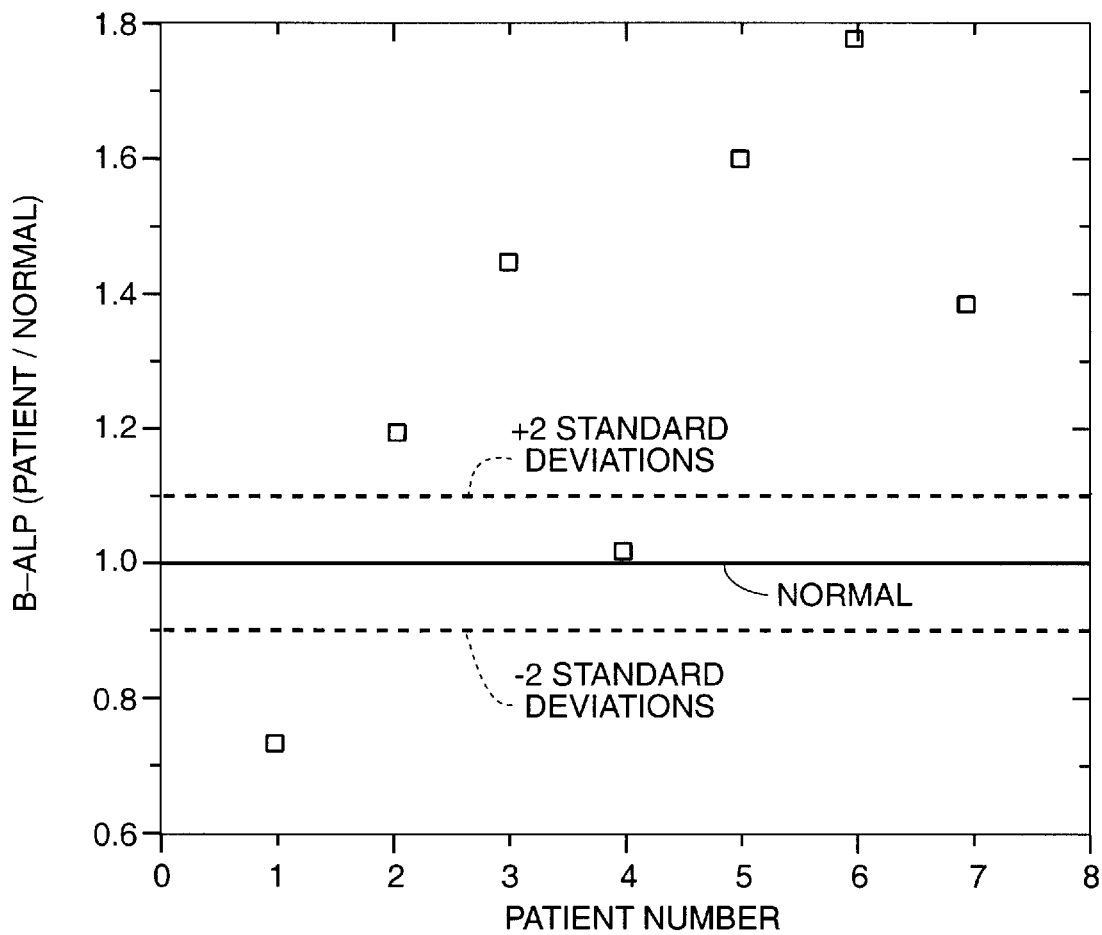
FIG._8

ASSAY FOR BONE ALKALINE PHOSPHATASE

BACKGROUND OF THE INVENTION

1. Field of the Invention

Osteoporosis is one of the most widespread diseases. This disorder is characterized by a decrease in bone mass leading to a weakening of the bone. The degree of weakening can be severe enough to result in fractures occurring spontaneously or a result of minor trauma.

There is a continuing need to develop therapeutics for the management of osteoporosis and other metabolic bone diseases. In order to develop and evaluate such drugs, a convenient and accurate means by which bone turnover can be monitored must be available. Currently, the diagnosis of osteoporosis depends on radiological and densitometric monitoring, bone biopsy examination and the assaying of bone specific biochemical markers.

Bone formation is monitored in serum through the use of biochemical markers by various assays including those for alkaline phosphatase, osteocalcin (bone Gla protein) or levels of the terminal extensions of procollagen.

Although the function of bone alkaline phosphatase ("B-ALP") in vivo is unknown, this isoenzyme is thought to be involved in bone formation. Several lines of evidence suggest that measurement of B-ALP activity in serum might prove a useful index of the bone formation rate:

(1) B-ALP is localized in the plasma membranes of osteoblasts, which are the bone-forming cells.

(2) In vitro studies have shown that the amount of alkaline phosphatase activity in fetal rat calvaria is proportional to the rate of collagen production. Canalis, *Metabolism* 32:14–20 (1983)

(3) In vivo studies with normal young mice have shown a correlation between serum alkaline phosphatase activity and osteoblast number. Marie, et al., *Calcif Tissue Int* 35:418–425 (1983)

(4) The amount of B-ALP activity in human serum is proportional to the rate of bone formation, at least when both are elevated as in young children and patients with Paget's disease. Farley, et al., *Metabolism* 35:563–571 (1986).

Since there is a critical demand for non-invasive measurements of bone formation and resorption rates, there is a need for a method of measuring B-ALP in serum as an index of the bone formation rate.

Ordinarily, human serum contains a variable mixture of related forms of alkaline phosphatase isoenzymes that can interfere with accurate assay results. These isoenzymes are derived from bone, kidney, intestinal, liver and placental tissues. Four different genes code for the main groups of alkaline phosphatase isoenzymes. Although the isoenzymes derived from the liver, kidney, and bone are the same gene product, they differ from each other on the basis of electrophoretic mobility and heat and urea stability. These differences are thought to be due to a post translational modification such as glycosylation.

One method of attempting to distinguish between the isoenzymes has been the use of monoclonal antibodies. However, most attempts to produce antibodies specific for B-ALP over liver alkaline phosphatase have resulted in cross reactive antibodies.

The present invention is directed to the monitoring of bone formation through the use of bone alkaline phosphatase.

More particularly, this invention concerns a method for determining the presence or amount of B-ALP in a sample using monoclonal antibodies that preferentially recognize B-ALP over the liver isoenzyme.

2. Description of the Related Art

Singh, et al., *Experimental Cell Research* 95:347–358 (1975) pertains to the use of antibodies to show that alkaline phosphatase from bone ("B-ALP") is a specific enzyme distinct from alkaline phosphatases from other sources.

Bailyes, et al, *Biochem. J.* 244:725–733 (1987) describes the preparation of B-ALP and liver alkaline phosphatase ("L-ALP") antibodies and their use in immunoaffinity purification of the enzymes.

Mulivor, et al., *J. Lab. Clin. Med.* 105(3):342–347 (1985) pertains to the use of monoclonal antibodies in immunoprecipitation of liver/bone/kidney, placental and intestinal alkaline phosphatase.

Hill, et al., European Patent Application No. 0381450 and *Clinica Chimica Acta* 186:315–320 (1989) pertain to monoclonal antibodies specific for B-ALP and not L-ALP, where one of the antibodies (BA1G 121) showed <3% cross-reactivity with L-ALP.

Hill, et al., Journal of Bone and Mineral Research 6:S244 (1991) describes an immunoradiometric assay for monitoring bone metastasis using monoclonal antibodies that are capable of distinguishing B-ALP from L-ALP.

Anderson, et al., U.S. Pat. No. 5,087,573 pertains to monoclonal antibodies that distinguish B-ALP from liver or kidney alkaline phosphatase.

Masuhara, et al., *International Orthopaedics* 15:61–64 (1991) describes an antibody (1B3.7) having about 3.5 fold greater binding to B-ALP than to L-ALP.

Seabrook, et al. *Clinica Chimica Acta* 172:261–266 (1988) pertains to a monoclonal antibody that exhibits 1.8 fold preference for B-ALP versus L-ALP.

Nagoya, et al. *Jpn. J. Cancer Research* 82:862–870 (1991) describes the detection of B-ALP by monoclonal antibodies that react with human osteosarcoma-associated antigen.

The art also describes antibodies that are specific to L-ALP over B-ALP. For example, Lawson, et al., *Clinical Chemistry* 31(3):381–385 (1985) pertains to a monoclonal antibody that exhibits a five-fold greater response with L-ALP than with B-ALP.

There are numerous references that pertain to assays for analytes with more than one epitope, in particular, assays that use two antibodies in a sandwich format. The following are illustrative of the state of the art.

Jeong, et al., U.S. Pat. No. 4,244,940 describes a sandwich assay useful for any ligand that can simultaneously become bound by two receptors.

Bunting, U.S. Pat. No. 4,271,140 pertains to a double receptor assay using a receptor complex comprised of a binding ligand, a receptor for the binding ligand and a receptor for the analyte.

Murad, et al., U.S. Pat. No. 4,474,892 describes a sandwich assay using two antibodies that are of a different class or subclass.

Forrest, et al., U.S. Pat. No. 4,659,678 pertains to an assay for an antigen with multiple epitopes using a reagent consisting of an antibody that is conjugated to a hapten or antigenic substance, where an antibody that binds the reagent, is bound to a support.

Schurrs, et al., U.S. Pat. Reissue No. 32,696 describes a sandwich assay where one reactant is bound to a support and one reactant is bound to an enzyme;

Zahradnik, et al., U.S. Pat. No. 4,935,339 pertains to an assay using a first monoclonal antibody, and a second different monoclonal antibody or a polyclonal antibody of restricted specificity, and a high affinity ligand for separation.

Gallati, et al., U.K. Patent Application No. 2,074,727 describes an assay for an antigen using two antibodies from different clones, which are directed towards different epitopes of the antigen.

Tanaka, et al., U.K. Patent Application No. 2,190,490 pertains to an assay using two antibodies that are from different animal species.

SUMMARY OF THE INVENTION

This invention relates to a method for determining the presence of bone alkaline phosphatase ("B-ALP") in a sample suspected of containing B-ALP, which comprises: (a) bringing together in an aqueous medium: the sample, a first antibody capable of specifically binding to a first epitopic site on B-ALP, and a second antibody capable of specifically binding to a second epitopic site on B-ALP, wherein the first and second epitopic sites are different and the first and second antibodies together form an immunocomplex with B-ALP, if present; and (b) examining the medium for the presence of the immunocomplex, the presence thereof being related to the presence of B-ALP in the medium. The first and second antibodies are different and are selected from the group consisting of a monoclonal antibody capable of binding to the epitopic site recognized by a monoclonal antibody produced by hybridoma cell line ATCC No. HB 11106, a monoclonal antibody capable of binding to the epitopic site recognized by a monoclonal antibody produced by hybridoma cell line ATCC No. HB 11107, and a monoclonal antibody capable of binding to the epitopic site recognized by a monoclonal antibody produced by hybridoma cell line ATCC No. HB 11108.

This invention also pertains to a method for determining the presence of B-ALP in a sample suspected of containing B-ALP, which comprises: (a) bringing together in an aqueous medium: the sample, a first antibody capable of specifically binding to a first epitopic site on B-ALP, and a second antibody capable of specifically binding to a second epitopic site on B-ALP, wherein the first and second epitopic sites are different and the first and second antibodies together form an immunocomplex with B-ALP, if present; and (b) examining the medium for the presence of the immunocomplex, the presence thereof being related to the presence of B-ALP in the medium. The first and second antibodies are from different cell lines and are selected from the group consisting of a monoclonal antibody produced by hybridoma cell line ATCC No. HB 11106, a monoclonal antibody produced by hybridoma cell line ATCC No. HB 11107, and a monoclonal antibody produced by hybridoma cell line ATCC No. HB 11108.

This invention also pertains to a method for detecting a bone disease in a patient suspected of having the disease, which comprises: (a) bringing together in an aqueous medium: a sample from the patient, a first antibody capable of specifically binding to a first epitopic site on B-ALP, and a second antibody capable of specifically binding to a second epitopic site on B-ALP, wherein the first and second epitopic sites are different and the first and second antibodies together form an immunocomplex with B-ALP, if present in said sample; examining the medium for the presence of the immunocomplex; and relating the presence of the immunocomplex to the presence of a bone formation disease in the patient. The first and second antibodies are different and are selected from the group consisting of a monoclonal antibody capable of binding to the epitopic site recognized by a monoclonal antibody produced by hybridoma cell line ATCC No. HB 11106, a monoclonal antibody capable of binding to the epitopic site recognized by a monoclonal antibody produced by hybridoma cell line ATCC No. HB 11107, and a monoclonal antibody capable of binding to the epitopic site recognized by a monoclonal antibody produced by hybridoma cell line ATCC No. HB 11108.

This invention also pertains to an improvement in a method for determining the presence of B-ALP in a sample suspected of containing B-ALP, which method comprises: bringing together in an aqueous medium the sample, a first antibody and a second antibody whereby an immunocomplex is formed with the first and second antibodies and B-ALP, if present; and examining the medium for the presence of the immunocomplex, the presence thereof being related to the presence of B-ALP in the medium. The improvement comprises selecting the first and second antibodies from the group consisting of a monoclonal antibody capable of binding to the epitopic site recognized by a monoclonal antibody produced by hybridoma cell line ATCC No. HB 11106, a monoclonal antibody capable of binding to the epitopic site recognized by a monoclonal antibody produced by hybridoma cell line ATCC No. HB 11107, and a monoclonal antibody capable of binding to the epitopic site recognized by a monoclonal antibody produced by hybridoma cell line ATCC No. HB 11108, with the proviso that said first and second antibodies are different. Alternatively, the improvement comprises selecting the first and second antibodies from the group consisting of a monoclonal antibody produced by hybridoma cell line ATCC No. HB 11106, a monoclonal antibody produced by hybridoma cell line ATCC No. HB 11107, and a monoclonal antibody produced by hybridoma cell line ATCC No. HB 11108, with the proviso that the first and second antibodies are from different cell lines.

This invention also relates to a method for determining the presence of B-ALP in a sample suspected of containing B-ALP, which comprises: bringing together in an aqueous medium, the sample, a first monoclonal antibody capable of binding to the epitopic site recognized by a monoclonal antibody produced by hybridoma cell line ATCC No. HB 11106, and a second monoclonal antibody capable of binding to the epitopic site recognized by a monoclonal antibody produced by hybridoma cell line ATCC No. HB 11107, and a third monoclonal antibody capable of binding to the epitopic site recognized by a monoclonal antibody produced by hybridoma cell line ATCC No. HB 11108, wherein the first, second and third antibodies are different, and two of the antibodies together form an immunocomplex with B-ALP, if present; and examining the medium for the presence of the immunocomplex, the presence thereof being related to the presence of B-ALP in the medium. At least one of the antibodies is detectably labeled or capable of being detectably labeled and at least one of the antibodies is bound to a support or capable of being bound to a solid support.

This invention also pertains to a method for determining the presence of B-ALP in a sample suspected of containing B-ALP, which comprises: bringing together in an aqueous medium, the sample, a first monoclonal antibody produced by hybridoma cell line ATCC No. HB 11106, and a second monoclonal antibody produced by hybridoma cell line ATCC No. HB 11107, and a third monoclonal antibody produced by hybridoma cell line ATCC No. HB 11108, wherein the first, second and third antibodies are different, and two of the antibodies together form an immunocomplex with B-ALP, if present; and examining the medium for the presence of the immunocomplex, the presence thereof being related to the presence of B-ALP in the medium. At least one of the antibodies is detectably labeled or capable of being detectably labeled and at least one of the antibodies is bound to a support or capable of being bound to a solid support.

This invention further relates to a kit for use in an assay method, comprising in a packaged combination in predetermined ratios for combination with a sample according to the assay method: a first antibody selected from the group consisting of a monoclonal antibody capable of binding to the epitopic site recognized by a monoclonal antibody produced by hybridoma cell line ATCC No. HB 11106, a monoclonal antibody capable of binding to the epitopic site recognized by a monoclonal antibody produced by hybridoma cell line ATCC No. HB 11107, and a monoclonal antibody capable of binding to the epitopic site recognized by a monoclonal antibody produced by hybridoma cell line ATCC No. HB 11108; and a second antibody selected from the group consisting of a monoclonal antibody capable of binding to the epitopic site recognized by a monoclonal antibody produced by hybridoma cell line ATCC No. HB 11106, a monoclonal antibody capable of binding to the epitopic site recognized by a monoclonal antibody produced by hybridoma cell line ATCC No. HB 11107, and a monoclonal antibody capable of binding to the epitopic site recognized by a monoclonal antibody produced by hybridoma cell line ATCC No. HB 11108. The antibodies are different.

This invention relates to another kit for use in an assay method, comprising in a packaged combination in predetermined ratios for combination with a sample according to the assay method: a first antibody selected from the group consisting of a monoclonal antibody produced by hybridoma cell line ATCC No. HB 11106, a monoclonal antibody produced by hybridoma cell line ATCC No. HB 11107, and a monoclonal antibody produced by hybridoma cell line ATCC No. HB 11108; and a second antibody selected from the group consisting of a monoclonal antibody produced by hybridoma cell line ATCC No. HB 11106, a monoclonal antibody produced by hybridoma cell line ATCC No. HB 11107, and a monoclonal antibody produced by hybridoma cell line ATCC No. HB 11108. The first and second antibodies are selected from different cell lines.

This invention further relates to monoclonal antibodies produced by hybridoma cell lines ATCC No. HB 11106, ATCC No. HB 11107, and ATCC No. HB 11108, which antibodies bind to epitopic sites on B-ALP.

DESCRIPTION OF THE DRAWING

FIG. 1 is a graphical representation of the epitope map of bone alkaline phosphatase.

FIG. 2 is a graph depicting the standard curve performed using affinity purified B-ALP.

FIG. 3 is a graph depicting the B-ALP standard curve in buffer.

FIG. 4 is a graph depicting the correlation of calculated B-ALP concentration versus spiked.

FIG. 5 is a graph depicting the cross-reactivity of the monoclonal antibodies with L-ALP.

FIG. 6 is a graph depicting the B-ALP levels in sera from patients with Paget's disease.

FIG. 7 is a graph depicting the B-ALP levels in sera from liver patients.

FIG. 8 is a graph depicting the B-ALP levels in sera from patients with untreated osteoporosis.

DESCRIPTION OF THE SPECIFIC EMBODIMENTS

This invention relates to monoclonal antibodies that are capable of binding to the epitopic sites recognized by the monoclonal antibodies produced by:

hybridoma cell line ATCC No. HB 11106;
hybridoma cell line ATCC No. HB 11107; and
hybridoma cell line ATCC No. HB 11108.

More particularly, these antibodies preferably bind to B-ALP and not L-ALP and exhibit cross-reactivity of less than 1%. This invention also relates to monoclonal antibodies produced by these hybridomas cell lines, in particular the monoclonal antibodies designated as B-ALP XI-4G6, B-ALP XI-10E3 and B-ALP XII-3B2.

Before proceeding further with the description of the specific embodiments of the present invention, a number of terms will be defined.

Member of a specific binding pair ("sbp" member): one of two different molecules, having an area on the surface or in a cavity that specifically binds to and is therefore defined as complementary with a particular spatial and polar organization of the other molecule. The members of the sbp can be referred to as ligand and receptor such as members of an immunological pair, e.g., antigen-antibody. As used herein, the term "ligand" refers to any organic compound for which a receptor naturally exists or can be prepared and the term "receptor" refers to any compound or composition capable of recognizing a particular spatial and polar organization of a molecule, i.e., epitopic or determinant site. Illustrative receptors include naturally occurring receptors, e.g., thyroxine binding globulin, antibodies, enzymes, Fab fragments, lectins, nucleic acids, protein A, complement component C1q, and the like. Other specific binding pairs which are not immunological pairs are also included in this invention, for example, biotin-avidin, hormones-hormone receptors, nucleic acid duplexes, IgG-protein A, DNA-DNA, DNA-RNA, and the like. Complementary sbp members bind to one another, as for example, a ligand and its complementary receptor.

Small molecule: a small molecule or a residue of a small molecule, having a molecular weight of from 100 to 2000, preferably 150 to 1000, for which a receptor exists or can be prepared. Examples of such small molecules include derivatives of biotin, lysergic acid, fluorescein or a fluorescein derivative, and vitamin $B_{12}$, when the corresponding receptors are avidin or streptavidin, anti-lysergic acid, anti-fluorescein and intrinsic factor, respectively.

Sample pretreatment: an optional step in an assay, designed to make bone alkaline phosphatase more readily available to one or more of the assay reagents or to reduce interference in the assay by sample components. Samples to be analyzed by the method of the present invention may be pretreated to: separate or lyse cells; precipitate, hydrolyse or denature proteins; hydrolyze lipids; solubilize analyte; or the like. Such pretreatment may include, without limitation: centrifugation; treatment of the sample with an organic solvent, for example, an alcohol, preferably an alcohol having less than about 7 carbon atoms such as methanol; and treatment with detergents, for example, sodium hydroxide.

Support or surface: a porous or non-porous water insoluble material. The surface can have any one of a number of shapes, such as strip, rod, particulate, including beads, liposomes, cells, sols and the like. Typical supports or surfaces include glass or plastic beads; latex or cellulose particles; bibulous materials such as porous membranes, glass or cellulose paper, and nitrocellulose membranes; polystyrene plates; magnetic particles; plastic tubes or vessels, and the like. The surface can be hydrophilic or capable of being rendered hydrophilic and can be formed from inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass, ceramics, metals, and the like.

Binding of sbp members, including the antibodies of this invention, to the surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970).

The receptor can be directly bonded, either covalently or non-covalently, to the surface of the support in such a manner as to permit ready binding of the conjugate containing a small molecule complementary to the receptor. Bonding of a receptor to the surface will normally be achieved by incubating the surface with the receptor, wherein the surface may previously have been treated with a reagent to enhance binding such as polycations, for example, polylysine; carbodiimides; silylating agents; bifunctional cross linking reagents such as carbonyl diimidazole; periodate; and similar activating reagents. Alternatively, the receptor can be indirectly bound to the support by first preparing the support with a compound complementary to the receptor such as an antibody against the receptor or by preparing the support with a receptor to a small molecule conjugated to the monoclonal antibody, for example, avidin coated beads and biotinylated antibodies.

Suitable particles are at least about 50 nm and not more than about 50 microns, usually at least about 100 nm and less than about 25 microns, preferably from about 0.2 to 5 microns in diameter. The particles may be organic or inorganic and preferably have a density approximating water, generally from about 0.7 to about 1.5 g/ml, and composed of material that can be transparent, partially transparent, or opaque. The particles may or may not have a charge, and when they are charged, they are preferably negative. The particles may be solid (e.g., polymer, metal, glass, organic and inorganic such as minerals, salts and diatoms), oil droplets (e.g., hydrocarbon, fluorocarbon, silicon fluid), or vesicles (e.g., synthetic such as phospholipid or natural such as cells and organelles). The particles may be latex particles or other particles comprised of organic or inorganic polymers; lipid bilayers, e.g., liposomes, phospholipid vesicles; oil droplets; silicon particles; metal sols; cells; and dye crystallites.

Organic particles will normally be polymers, either addition or condensation polymers, which are readily dispersible in the assay medium. The organic polymers will also be adsorptive or functionalizable so as to bind, either directly or indirectly, an sbp member.

The particles can be derived from naturally occurring materials, naturally occurring materials which are synthetically modified and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like. Inorganic polymers include silicones, glasses, available as Bioglas, and the like. Natural or synthetic assemblies such as liposomes, phospholipid vesicles, and cells can also be employed.

Where the particles are commercially available, the particle size may be varied by breaking larger particles into smaller particles by mechanical means, such as grinding, sonication, agitation, etc.

When the support is a matrix of beads, the beads are usually non-porous, usually glass or latex an normally are 0.2–2.5 mm average in diameter. Most preferably, the beads are 0.5–2 mm average in diameter. The beads are usually approximately spherical and may have a rough or smooth surface. Because of the high surface area of beads, attention must be paid to the surface properties so that background nonspecific binding remains low. Where avidin is used as the receptor bound to the beads, non-specific binding can be reduced by drying the glass beads in the presence of sucrose after the binding of avidin to the beads. Examples of coatings in addition to the sugars, which have been found to be useful includes bovine serum albumin, poly(vinyl alcohol), casein and non-fat milk.

The support or surface will usually be polyfunctional or be capable of being polyfunctionalized or be capable of binding a receptor such as the antibodies of the invention through specific or non-specific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to particles is well known and is amply illustrated in the literature. See for example Cuatrecasas, *J. Biol. Chem.*, 245:3059 (1970). The length of a linking group to the material being linked may vary widely, depending upon the nature of the material being linked, the effect of the distance between the material being linked and the surface, on the binding of antibodies and B-ALP, and the like.

Signal producing system ("sps"): one or more components, at least one component being a label, which generate a detectable signal that relates to the amount of bound and/or unbound label, i.e. the amount of label bound or not bound to the B-ALP being detected or to an antibody against B-ALP. The "sps" includes all the reagents required to produce a detectable signal. There are numerous methods by which the label can produce a detectable signal, for example by electromagnetic radiation, heat, chemical reagents, and the like.

The label can directly produce a signal, i.e., additional reagents are not required to produce a signal. For example, numerous organic molecules are able to absorb ultraviolet and visible light, where the light absorption transfers energy to these molecules and elevates them to an excited energy state. This absorbed energy is then dissipated by emission of light at a second wavelength. For example, fluorescent molecules are able to absorb light at one wavelength and emit light at a second wavelength. Suitable fluorescent molecules include fluorescein, isothiocyanate, rhodamine, phycoerythrin, phycocyanin, allophycocyanin, o-phthaldehyde, and fluorescamine. A large number of illustrative fluorescers are indicated in Litman, et al., U.S. Pat. No. 4,275,149, columns 30 and 31, which disclosure is incorporated herein by reference. Other examples of labels that can directly produce a signal are radioactive isotopes, such as $^{125}I$, $^{131}I$, $^{14}C$, $^{3}H$, $^{57}Co$ and $^{75}Se$, and the like; and dyes, such as are well known in the art.

Alternately, the label may also require other reagents in order to produce a signal. Therefore, the signal producing system includes all of the reagents required to produce a measurable signal including a first sbp member when conjugated to a label and the components of the developer. When the first sbp member is not conjugated to a label, the label is normally bound to an sbp member complementary to the first sbp member and is usually included as part of the developer. Other components of the developer include substrates, coenzymes, enhancers, second enzymes, activators, cofactors, inhibitors, scavengers, metal ions, specific binding substance required for binding of signal generating substances, and the like. Some of the chemical reagents such as coenzymes, substances that react with enzymic products, other enzymes and catalysts, and the like can be bound to other molecules or to a support.

The signal producing system provides a signal detectable by external means, normally by measurement of electromagnetic radiation, desirably by visual examination. For example, the signal producing system can include a chromophoric substrate and enzyme, where the chromophoric substrate is enzymatically converted to a dye that absorbs light in the ultraviolet or visible region, phosphors or fluorescers.

The signal-producing system can include at least one catalyst, usually at least one enzyme, and at least one substrate and may include two or more catalysts and a plurality of substrates, and may include a combination of enzymes, where the substrate of one enzyme is the product of the other enzyme. The operation of the signal producing system is to produce a product that provides a detectable signal related to the amount of catalyst bound to the support, as a result of sbp member complex formation of the labeled sbp member.

The signal producing system provides for the production of a compound, which is normally the signal generating compound, but in some instances may react with another compound bound to the surface with the production, enhancement or destruction of the signal generating compound. While both enzymatic and non-enzymatic catalysts may be employed, usually there will be at least one enzyme catalyst employed in the signal producing system. In the event of there being only one catalyst, this catalyst will usually be conjugated to an sbp member through sbp member complex formation. In addition to the catalyst, there must be a substrate that undergoes a transformation, which results in a change in a detectable signal at the measurement surface. For the most part, the product resulting from the transformation catalyzed by the labeled sbp member will be the signal generating compound.

Two catalysts may be employed, either a combination of an enzyme and a non-enzyme catalyst or two enzymes, where the two catalysts are related in that the product of one is the substrate of the other. In this system, there need be only one substrate that can undergo successive changes catalyzed by the catalysts, which results in the compound involved with production of a detectable signal. For the most part, however, there will normally be a substrate for the first enzyme in the series and a second compound, which serves as a precursor to the compound involved in the production of the signal, normally providing the compound that produces the signal. Thus, the product of the first enzyme may react with the precursor to the signal producing compound to provide the signal generating compound.

For the most part, the involved reactions will be hydrolysis or redox reactions. In the case of hydrolysis, a derivatized dye precursor that has an enzymatically labile bond and an enzyme that catalyzes its conversion to an insoluble dye product is illustrative of this type of system. In redox reactions, a first enzyme would produce an essential oxidizing substrate for the second enzyme, where the second enzyme catalyzes the reaction between the oxidizing substrate and a dye precursor.

Where two enzymes are used, the first enzymatic reaction may involve hydrolytic cleavage or a redox reaction of the substrate to provide a product that is the substrate of another enzyme. The first situation may be illustrated by glucose-6-phosphate being catalytically hydrolyzed by alkaline phosphatase to glucose, where glucose is a substrate for glucose oxidase. The second situation may be illustrated by glucose being oxidized by glucose oxidase to provide hydrogen peroxide that would enzymatically react with a leuco dye to produce a signal generator.

Coupled catalysts can also involve an enzyme with a non-enzymatic catalyst. The enzyme can produce a reactant that undergoes a reaction catalyzed by the non-enzymatic catalyst or the non-enzymatic catalyst may produce a substrate (includes coenzymes) for the enzyme. A wide variety of non-enzymatic catalysts that may be employed are found in Ullman, U.S. Pat. No. 4,160,645, the appropriate portions of which are incorporated herein by reference.

Various combinations of enzymes may be employed to provide a signal generating compound. Particularly, combinations of hydrolases may be employed to produce an insoluble signal generator. Alternatively, combinations of hydrolases and oxidoreductases can provide the signal generating compound.

For combinations of enzymes one enzyme can be non-diffusively bound to the capillary tube, while the other enzyme is conjugated to a sbp member. Additionally, one or more other members of the signal producing system can be bound to the tube depending on the particular signal producing system chosen or the particular protocol followed.

Because of the nature of the signal, in order to have a detectable signal, it is desirable to provide means for amplifying the signal produced by the presence of the label. Therefore, it will usually be preferable for the label to be a catalyst or luminescent compound, most preferably a catalyst. Preferable catalysts are enzymes and coenzymes, which can produce a multiplicity of signal generating molecules from a single label.

An enzyme or coenzyme is employed that provides the desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in Litman, et al., U.S. Pat. No. 4,275,149 bridging columns 19 to 23, and Boguslaski, et al., U.S. Pat. No. 4,318,980, columns 10 to 14, which disclosures are incorporated herein by reference.

Of particular interest is the use of a combination of enzymes, where the enzymes are related by the product of one enzyme being the substrate of the other enzyme. In this manner, stable precursors to labile substrates can be provided and the substrate for a second enzyme can be stored in combination with a first enzyme without a reaction being prematurely initiated.

A number of enzyme combinations are set forth in Litman, et al., U.S. Pat. No. 4,275,149, bridging columns 23 to 28, which combinations can find use in the subject invention. This disclosure is incorporated herein by reference.

Of particular interest are enzymes that involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme that employs the hydrogen peroxide to oxidize a dye precursor, i.e., a peroxidase such as horseradish peroxidase, lactoperoxidase, and microperoxidase. Additional enzyme combinations may be found in the subject matter incorporated by reference.

When a single enzyme is used as a label, other enzymes may find use such as hydrolases, transferases, and oxidoreductases preferably hydrolases such as alkaline phosphatase and β-galactosidase. Alternatively, luciferases may be used such as firefly luciferase and bacterial luciferase.

Illustrative coenzymes that find use include NAD [H]; NADP [H], pyridoxal phosphate; FAD [H]; FMN [H], etc., usually coenzymes involving cycling reactions, see particularly U.S. Pat. No. 4,318,980.

The product of the enzyme reaction will usually be a dye or fluorescer. A large number of illustrative fluorescers are indicated in Litman, et al., U.S. Pat. No. 4,275,149, columns 30 and 31, which disclosure is incorporated herein by reference.

Chemiluminescent compounds are also suitable as labels such as, by means of illustration and not limitation, luminol, isoluminol, aromatic acridinium esters, imidazole, acridinium salt, oxalate ester, and the like. Numerous chemiluminescers are set forth in Litman, et al., U.S. Pat. No. 4,275,149, column 31, which disclosure is incorporated herein by reference. Chemiluminescers can also be used in conjunction with photosensitizers, such as is described in U.S. Ser. No. 07/704,569, filed May 22, 1991 entitled "Assay Method Utilizing Induced Luminescence", which disclosure is incorporated herein by reference.

Ancillary Materials: Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

As indicated above, this invention relates to antibodies that specifically bind to epitopic sites defined by the monoclonal antibodies produced by:

hybridoma cell line ATCC No. HB 11106;
hybridoma cell line ATCC No. HB 11107; and
hybridoma cell line ATCC No. HB 11108.

Monoclonal antibodies produced by these hybridoma cell lines are capable of binding to epitopic sites on B-ALP. In particular, these antibodies preferably bind to B-ALP and not L-ALP and exhibit cross-reactivity with L-ALP of less than 1%. Based upon their ability of compete with each other for binding to B-ALP, it was found that these monoclonal antibodies bind to different epitopic sites on B-ALP.

The monoclonal antibodies of this invention are essentially obtained by a process similar to that described in Milstein and Kohler, *Nature* 256:495–497 (1975). The details of the Milstein and Kohler process are well established. Generally, the process involves injecting a host, usually a mouse or other suitable animal, with an immunogen. Cells are then taken from the spleen of the animal. Alternatively, the host may be unsensitized spleen cells, which are sensitized to the immunogen in vitro. The resulting cells are fused with myeloma cells. The result is a hybrid cell, referred to as a "hybridoma" that can be cultured in vitro. The population of hybridomas is screened and manipulated so as to isolate individual clones, each of which secretes a single antibody to the antigen.

The immunogen used to obtain the antibodies of the present is bone alkaline phosphatase ("B-ALP"), which is obtained form a source high in B-ALP, such as a human osteosarcoma cell. The antibodies of the present invention are capable of specifically recognizing B-ALP and not recognizing closely related compounds such as liver alkaline phosphatase ("L-ALP").

When the immunogen is introduced into the host, the host's immune system responds by producing a variety of antibodies that are able to recognize various sites on the immunogen. These numerous antibodies have different affinities and specificities. To obtain those antibodies that have desirable affinity and specificity traits for the particular assay method being used, the different hybridoma cell lines are screened.

As mentioned above, the present invention pertains to monoclonal antibodies that are highly specific for B-ALP, especially in the presence of L-ALP. Preferred embodiments of this aspect of the invention include antibodies B-ALP XI-4G6, B-ALP XI-10E3 and B-ALP XII-3B2. The hybridomas that produce antibodies B-ALP XI-4G6, B-ALP XI-10E3 and B-ALP XII-3B2, which are referred to by the designation of the antibody that they produce, were deposited with the American Type Culture Collection ("ATCC") (Rockville, Maryland) as follows:

| Hybridoma | Deposit Date | Accession Number |
| --- | --- | --- |
| B-ALP XI-4G6 | August 27, 1992 | HB 11106 |
| B-ALP XI-10E3 | August 27, 1992 | HB 11107 |
| B-ALP XII-3B2 | August 27, 1992 | HB 11108 |

Antibodies that compete with a monoclonal antibody produced by one of these hybridoma cell lines, are said to be capable of specifically binding to the epitopic site defined by the monoclonal antibodies produced by that cell line.

As mentioned above, the present invention concerns a method for determining the presence or amount of bone alkaline phosphatase ("B-ALP") in a sample. In particular, this method uses at least two different highly specific monoclonal antibodies that are capable of recognizing B-ALP and not liver alkaline phosphatase ("L-ALP").

As indicated above, the monoclonal antibodies of this invention are capable of binding to the epitopic site recognized by a monoclonal antibody produced by hybridoma cell line ATCC No. HB 11106, or are capable of binding to the epitopic site recognized by a monoclonal antibody produced by hybridoma cell line ATCC No. HB 11107, or are capable of binding to the epitopic site recognized by a monoclonal antibody produced by hybridoma cell line ATCC No. HB 11108.

Alternatively, the monoclonal antibodies of this invention are produced by hybridoma cell line ATCC No. HB 11106, or produced by hybridoma cell line ATCC No. HB 11107, or produced by hybridoma cell line ATCC No. HB 11108.

These monoclonal antibodies are useful in a variety of assay formats, which are described in detail below. When more that one monoclonal antibody is used, they must be different so as to bind to different epitopic sites. An example of this is where the first antibody is capable of binding to the epitopic site recognized by a monoclonal antibody produced by hybridoma cell line ATCC No. HB 11106 and the second antibody is capable of binding to the epitopic site recognized by a monoclonal antibody produced by hybridoma cell line ATCC No. HB 11107. Another example is where the first antibody is produced by hybridoma cell line ATCC No. HB 11107 and the second antibody is produced by hybridoma cell line ATCC No. HB 11108. Yet another example is where the first antibody is produced by hybridoma cell line ATCC No. HB 11106 and the second antibody is capable of binding to the epitopic site recognized by a monoclonal antibody produced by hybridoma cell line ATCC No. HB 11108.

The monoclonal antibodies of this invention may be adapted to most assays involving sbp members such as ligand-receptor, e.g., antigen-antibody reactions. The assays may be homogeneous or heterogeneous, competitive or sandwich. The sample may be pretreated if necessary to remove unwanted materials. The immunological reaction for a sandwich type assay usually involves an sbp member, e.g., a monoclonal antibody of the invention, that is bound to a label, a second sbp member, e.g., a different monoclonal antibody of the invention, and the sample of interest. In a competitive protocol the label may be associated with an sbp member that is analogous to, usually a derivative of, B-ALP.

After all of the reagents have been combined, they can be incubated, if desired. In a homogeneous assay, the sps members are then activated and the resulting signal is measured. For example, if the sps members are an enzyme label and its substrate, substrate is added and the signal produced is related to the amount of B-ALP in the sample tested. In a heterogeneous assay, the unlabeled sbp member is bound or can be caused to bind to a support, which may be a surface or a particle having a label. These materials are generally combined either simultaneously or wholly or partially sequentially. The support is then separated from the liquid phase and either the solid phase or the liquid phase is examined for the presence of a signal.

For a more detailed discussion of the above immunoassay techniques, see "Enzyme-Immunoassay," by Edward T. Maggio, CRC Press, Inc., Boca Raton, Fla., 1980. See also, for example, U.S. Pat. Nos. 3,690,834; 3,791,932; 3,817, 837; 3,850,578; 3,853,987; 3,867,517; 3,901,654; 3,935, 074; 3,984,533; 3,996,345; and 4,098,876, which listing is not intended to be exhaustive.

In particular, the monoclonal antibodies of this invention are useful in a sandwich assay for the determination of the presence of B-ALP in a sample suspected of containing B-ALP. The following are brought together in an aqueous medium: the sample, a first antibody capable of specifically binding to a first epitopic site on B-ALP, and a second antibody capable of specifically binding to a second epitopic site on B-ALP. The first and second epitopic sites are different and the first and second antibodies together form an immunocomplex with B-ALP, if present. The medium is then examined for the presence of the immunocomplex, the presence thereof being related to the presence of B-ALP in the medium.

The monoclonal antibodies described herein are also useful in a method for detecting a bone disease in a patient suspected of having the disease. A sample from the patient, a first antibody capable of specifically binding to a first epitopic site on B-ALP, and a second antibody capable of specifically binding to a second epitopic site on B-ALP, are brought together in an aqueous medium. The first and second epitopic sites are different and the first and second antibodies together form an immunocomplex with B-ALP, if present in the sample. The medium is then examined for the presence of the immunocomplex and the presence of the immunocomplex is then related to the presence of a bone formation disease in the patient.

In the aforementioned methods, at least one of the antibodies will preferably be labeled or capable of being detectably labeled. Illustrative of an antibody that is capable of being detectably labeled, is an antibody that is bound to a first specific binding pair member. A second specific binding pair member, which is complementary to the first specific binding pair member, is bound to a detectable label. Such a situation is also referred to as indirect labeling.

In addition, in the aforementioned methods, one of the antibodies can be bound to a support or capable of being bound to a solid support. Similarly, illustrative of an antibody that is capable of being bound to a support, is an antibody that is bound to a first specific binding pair member. A second specific binding pair member, which is complementary to the first specific binding pair member, is bound to a solid support.

This invention also pertains to using the monoclonal antibodies of the invention in an improvement in the art involving a method for determining the presence of B-ALP in a sample suspected of containing B-ALP, which comprises: bringing together in an aqueous medium the sample, a first antibody and a second antibody whereby an immunocomplex is formed with the first and second antibodies and B-ALP, if present; and examining the medium for the presence of the immunocomplex, the presence thereof being related to the presence of B-ALP in the medium. In one embodiment of the improvement, the antibodies are selected from the group consisting of a monoclonal antibody capable of binding to the epitopic site recognized by a monoclonal antibody produced by hybridoma cell line ATCC No. HB 11106, a monoclonal antibody capable of binding to the epitopic site recognized by a monoclonal antibody produced by hybridoma cell line ATCC No. HB 11107, and a monoclonal antibody capable of binding to the epitopic site recognized by a monoclonal antibody produced by hybridoma cell line ATCC No. HB 11108. The first and second antibodies are different. In another embodiment of the improvement, the antibodies are selected from the group consisting of a monoclonal antibodies produced by hybridoma cell lines ATCC No. HB 11106, ATCC No. HB 11107, and ATCC No. HB 11108, with the proviso that the first and second antibodies are from different cell lines.

Another aspect of this invention involves using three monoclonal antibodies of the invention in a method for determining the presence of B-ALP in a sample suspected of containing B-ALP, which comprises bringing together in an aqueous medium: the sample, a first monoclonal antibody capable of binding to the epitopic site recognized by a monoclonal antibody produced by hybridoma cell line ATCC No. HB 11106, a second monoclonal antibody capable of binding to the epitopic site recognized by a monoclonal antibody produced by hybridoma cell line ATCC No. HB 11107, and a third monoclonal antibody capable of binding to the epitopic site recognized by a monoclonal antibody produced by hybridoma cell line ATCC No. HB 11108. These monoclonal antibodies are capable of specifically binding to different epitopic sites on B-ALP. Two of the antibodies together form an immunocomplex with B-ALP, if present, where at least one of the antibodies is detectably labeled or capable of being detectably labeled and at least one of the antibodies is bound to a support or capable of being bound to a solid support. The medium is then examined for the presence of the immunocomplex, the presence thereof being related to the presence of B-ALP in the medium. For example, two different monoclonal antibodies can be bound to a support, where they then bind any B-ALP present in the sample. A third, different monoclonal antibody, labeled directly or indirectly, then forms an immunocomplex with any bound B-ALP.

Another aspect of this invention involves using three monoclonal antibodies of the invention in a method for determining the presence of B-ALP in a sample suspected of containing B-ALP, which comprises bringing together in an aqueous medium: the sample, a first monoclonal antibody produced by hybridoma cell line ATCC No. HB 11106, a second monoclonal antibody produced by hybridoma cell line ATCC No. HB 11107, and a third monoclonal antibody produced by hybridoma cell line ATCC No. HB 11108. These monoclonal antibodies are capable of specifically binding to different epitopic sites on B-ALP. Two of the antibodies together form an immunocomplex with B-ALP, if present, where at least one of the antibodies is detectably labeled or capable of being detectably labeled and at least one of the antibodies is bound to a support or capable of being bound to a solid support. The medium is then examined for the presence of the immunocomplex, the presence thereof being related to the presence of B-ALP in the medium.

In one embodiment of this aspect of the invention, one of the antibodies is detectably labeled or capable of being detectably labeled and two of the antibodies are bound to a support or capable of being bound to a solid support.

In another embodiment of the invention, two of the antibodies are detectably labeled or capable of being detectably labeled and one of the antibodies is bound to a support or capable of being bound to a solid support.

For illustrative purposes, the monoclonal antibodies of the invention can be used in the following assay protocols where the analyte is B-ALP. These illustrations should not be construed as a limitation on the scope of the invention.

(A) In an assay for B-ALP, a monoclonal antibody of this invention, for example a monoclonal antibody produced by hybridoma cell line ATCC No. HB 11107, conjugated to glucose-6-phosphate dehydrogenase, is utilized. A serum sample is combined with the anti-B-ALP-G6PDH conjugate and a monoclonal antibody of this invention that binds to an epitopic site other than that recognized by the monoclonal antibody produced by cell line 11107, for example, a monoclonal antibody produced by hybridoma cell line ATCC No. HB 11108, bound to 1 micron latex particles. After incubation of the suspension for 30 minutes, the particles are separated from the medium by centrifugation, washed and suspended in an aqueous solution containing glucose-6-phosphate. The signal produced is directly related to the amount of B-ALP in the sample.

(B) In an assay for B-ALP in serum, a monoclonal antibody produced by hybridoma cell line ATCC No. HB 11107, conjugated to HRP is utilized. The sample is combined with the antibody-HRP conjugate and a monoclonal antibody capable of binding to the epitopic site recognized by a monoclonal antibody produced by hybridoma cell line ATCC No. HB 11108, which is bound to glass beads. The medium is incubated for 10 minutes and the beads separated and washed. The beads are then placed in an aqueous medium to which substrate is added. The signal produced is directly related to the amount of B-ALP in the sample.

These methods are merely illustrative of the qualitative, semi-quantitative and quantitative assay methods in which the monoclonal antibodies of this invention can be used for determining bone alkaline phosphatase in a sample. Where the B-ALP is to be detected in physiological fluids, the sample may include blood, serum, plasma, saliva, lymph or the like, but preferably is serum. Preferably, in carrying out the method of this invention, an aqueous medium will be employed. Other polar solvents may also be employed, usually oxygenated organic solvents of from 1–6, more usually from 1–4 carbon atoms, including alcohols, ethers and the like. Usually these cosolvents will be present in less than about 40 weight percent, more usually in less than about 20 weight percent.

While the order of addition of the various reagents may be varied widely, there will be certain preferences depending on the nature of the particular assay format being used. The reagents and sample can be combined simultaneously or wholly or partially sequentially with each other and the support. As used herein, the term "wholly or partially sequentially" means that, when the sample and various reagents utilized in the present invention are combined other than concomitantly (simultaneously), one or more of the reagents may be combined with one or more of the remaining reagents to form a subcombination. Each subcombination can then be combined and subjected to the methods described herein. Optionally, an incubation step may be involved after the reagents are combined, generally ranging from about 30 seconds to 6 hours, more usually from about 2 minutes to 1 hour. It is understood that there are certain sequences of steps that are more convenient and the choice of the particular sequence to be employed depends upon the selection of reagents and assay format and is not critical to the invention.

In the assays of the present invention, any convenient label can be used. The label can be bound covalently to a monoclonal antibody of this invention. Alternatively, the label can be bound to a receptor for a monoclonal antibody of this invention or to a receptor that is capable of binding to a small molecule conjugated to a monoclonal antibody of this invention, for example, labeled anti-fluorescein and fluorescein-labeled monoclonal antibody. This invention also permits the use of no label since, once the B-ALP is captured, its presence can be detected by reacting the captured complex with a substrate for B-ALP, such as p-nitrophenyl phosphate, or an orthophosphoric monoester.

Bonding of the label to a monoclonal antibody of this invention or to a receptor, may be accomplished by chemical reactions wherein the result is replacing a hydrogen of the label with a bond to the receptor or may include a linking group between the label and the receptor. The linking group may be of any size but preferably no larger than necessary to permit unfettered binding of a compound complementary to the compound bound to the label, and to permit interaction with the other members of the signal producing system, i.e. to permit signal production by the label. Generally, the linking group will be from 1 to 100 atoms, usually from 1 to 15 atoms. The linking group can be introduced into the label or receptor for attachment. A functionality for attachment such as carboxylic acid, hydroxyl, thio, amino, aldehydic, amido, activated ethylenes such as maleimide, sulfonic acids, and the like, can be introduced into the label or receptor, if the functionality is not originally present in the label or receptor. Methods of conjugation are well known in the art. See for example, U.S. Pat. No. 3,817,837, the disclosure of which is incorporated herein by reference.

The conjugates of this invention that utilize a small molecule capable of binding to a receptor, will contain small molecules for which a natural receptor exists or can be prepared. The small molecules will usually be neither extremely hydrophilic nor extremely hydrophobic and will preferably be structurally dissimilar to substances that are likely to be present in the sample. Conjugates of small molecules with antibodies will have at least one and frequently 2–20 small molecules in the conjugate which will usually be bound covalently. As described above with reference to the label-receptor bond, bonding of the small molecule to the antibody may be accomplished by chemical reactions which result in replacing a hydrogen atom of the small molecule with a bond to the antibody or may include a linking group between the small molecule and the antibody of any size but preferably no larger than necessary to permit binding to the conjugate of both a receptor for the small molecule and B-ALP.

As indicated above, numerous supports can be used in the assays described herein. Whatever type of solid support is used, it must be treated so as to have the monoclonal antibodies of this invention bound to its surface or a receptor bound to its surface, which receptor will specifically bind to the monoclonal antibodies of this invention or to a small molecule conjugated to the monoclonal antibody. For example, avidin can be covalently bound to spherical glass beads of 0.5–1.5 mm. A matrix of these beads is mixed in an aqueous medium with a biotinylated monoclonal antibody that specifically binds to an epitopic site defined by this invention, a sample suspected of containing B-ALP, and a labeled monoclonal antibody of the invention (where the biotinylated and labeled antibodies are different, i.e., bind to different epitopic sites on B-ALP). After sufficient incubation to permit binding of the antibodies to B-ALP and the biotinylated antibody to the beads, the solution is separated from the beads and washed. After sufficient washings, the label is detected and the amount of label is related to the amount of B-ALP in the sample. For example, if the label is an enzyme, substrate would be added and the amount of enzyme product determined photometrically after a suitable incubation time and compared to the amount of product provided, using a sample of known concentration of B-ALP.

In assays in accordance with the present invention, the pH for the medium will usually be in the range of about 4–11, more usually in the range of about 5–10, and preferably in the range of about 5.4–9.5. The pH is chosen so as to maintain a significant level of binding between sbp members, such as the monoclonal antibodies to B-ALP, while optimizing signal producing proficiency. In some instances, a compromise will be made between these two considerations. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the method and usually constant temperatures during the period of the method. The temperatures for the determination will generally range from about 10°–50° C., more usually from about 15°–40° C.

The concentration of B-ALP which may be assayed will generally vary from about $10^{-4}$ to $10^{-15}$ M, more usually from about $10^{-6}$ to $10^{-13}$ M. Considerations such as whether the assay is qualitative, semi-quantitative or quantitative, the particular detection technique, and the concentration of B-ALP will normally determine the concentration of the other reagents.

While the concentrations of the various reagents will generally be determined by the concentration range of interest of B-ALP, the final concentration of each of the reagents will normally be determined empirically to optimize the sensitivity of the assay over the range of interest.

The concentration of the monoclonal antibodies in the assay medium is dependent on the type of assay, heterogeneous or homogeneous, competitive or direct, etc. Normally, the monoclonal antibodies of the invention will be present in the assay medium in a concentration about 0.1 to 5 $\mu$g/ml, usually about 0.4 to 2 $\mu$g/ml.

As a matter of convenience, the antibodies and reagents for use in the present invention can be provided in a kit for use in an assay method. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. As a matter of convenience, the reagents employed in the present invention can be provided in predetermined amounts. The reagents will include a first antibody and a second antibody, which are selected from the group consisting of a monoclonal antibody capable of binding to the epitopic site recognized by a monoclonal antibody produced by hybridoma cell line ATCC No. HB 11106, a monoclonal antibody capable of binding to the epitopic site recognized by a monoclonal antibody produced by hybridoma cell line ATCC No. HB 11107, and a monoclonal antibody capable of binding to the epitopic site recognized by a monoclonal antibody produced by hybridoma cell line ATCC No. HB 11108. The first and second antibodies are different. Alternatively, the first and second antibodies can be selected from the group consisting of monoclonal antibodies produced by hybridoma cell lines ATCC No. HB 11106, ATCC No. HB 11107, and ATCC No. HB 11108, with the proviso that the first and second antibodies are from different cell lines.

The antibodies can be labeled or bound to a solid support, or capable of being labeled or bound to a solid support. The kit can further include other packaged reagents for conducting an assay including members of the signal producing system, such as the enzyme substrate and any cofactor, calibrators, ancillary reagents, and so forth.

The relative amounts of the various reagents may be varied widely, to provide for concentrations in solution of reagents, which substantially optimize the sensitivity of the assay. The reagents may be provided as dry powders, usually lyophilized, including excipients, which on dissolution will provide for a reagent solution having the appropriate concentrations for performing the assay.

EXAMPLES

The invention is demonstrated further by the following illustrative examples.

PREPARATION OF MATERIALS

Purification of Human Bone Alkaline Phosphatase

Human bone alkaline phosphatase ("B-ALP") was extracted from the SaOS-2 human osteosarcoma cell line (available from the American Type Culture Collection under Accession Number HTB 85). The cell line was maintained at a subconfluent density in Super Dulbecco's Modified Essential Medium ("S-DMEM") containing gentamycin and 10% fetal bovine serum ("FBS"). The cells were passaged by treatment with trypsin in ethylenediaminetetraacetic acid ("EDTA"). The culture medium was changed at 48–72 hour intervals. The cells were seeded in T-150 tissue culture flasks.

For fresh cells: After several days in culture, the medium was removed from the confluent culture and the cell layers were rinsed at least three times with phosphate buffered saline ("PBS") to ensure the removal of bovine serum ALP activity from the cells. The cells were then extracted with buffer (12.5 mM Tris-carbonate pH 6.8, 1% Triton-X 100, 1 mM $MgCl_2$ and Aprotinin (Sigma), phenylmethylsulfonylfluoride ("PMSF") and Pepstatin A (Sigma)). After 20 minutes of extraction, the extracted material was spun at 5000 rpm at 4° C. for 30 minutes. The supernatant fluid was collected and stored at 4° C.

For frozen cells, where the confluent culture had been trypsinized and frozen in 40% FCS, 20% dimethyl sulfoxide ("DMSO"), and 40% Dulbecco's Modified Essential Medium ("DMEM"): The frozen cells were thawed when needed, washed once with Super DMEM containing 10% FBS, and then three more times with PBS. Extraction was performed as described above.

Some of the supernatant cell extracts were then purified by (A) using Wheat Germ Agglutinin-Sepharose 6B beads (Sigma, "WGA-beads") and some were purified by (B) gel filtration followed by affinity purification:

(A) WGA-bead Purification of B-ALP

Since B-ALP is rich in sialic acid, WGA-beads were used to partially purify some of the cell extracts. WGA-beads were washed and then incubated with the cell extracts. After centrifugation and washing of the beads three times, elution of the bound materials was performed with N-acetylglucosamine.

Results of a Paragon gel analysis indicated that the starting materials and the bound material had alkaline phosphatase activity while the free materials and the washes did not.

(B) Gel Filtration/affinity Purification of B-ALP

The column volume used for the gel filtration of the remaining cell extracts was 85.7 ml (1.4×48.5 cm) and was packed with Sephacryl S-300 (superfine). The column was equilibrated with buffer (12.5 mM Tris carbonate, pH 6.8, 1 mM $MgCl_2$, 1% Triton X-100). 30-drop fractions were collected (volume=800 $\mu$l) per 300 seconds. Alkaline phosphatase activity was measured for each fraction. Activity was found in fractions that corresponded to a molecular weight of 90 k. A pool of the peak fractions showed only a few bands on a polyacrylamide gel electrophoresis.

The gel filtration purified B-ALP was then purified by immunoaffinity by use of the anti-alkaline phosphatase monoclonal antibodies obtained by the method described below. The monoclonal antibodies were coupled to Affigel 10 (Bio-Rad) activated agarose beads. The column was washed with 10 mM Tris, pH 7.3. The enzyme to be purified was applied several times on the column, followed by washing with 120 mM Tris, pH 7.3. The bound enzyme was eluted with 1.5 M of 2 amino-methyl propanol, pH 10.3, 3.0 M NaCl. The eluted enzyme was dialyzed against 10 mM Tris, pH 7.3, 1 mM $MgCl_2$.

Haptenating B-ALP

The purified B-ALP was lightly haptenated with trinitrobenzene sulfonic acid (Handbook of Experimental Immunology, D. M. Weir, ed., pages 29.3–29.4 ©01978, Blackwell Scientific Publications) to yield trinitrophenol-B-ALP ("TNP-B-ALP").

Bone alkaline phosphatase preparations (3.0 and 7.7 mg/ml) were reacted with an 8-fold molar excess of trinitrobenzene sulfonic acid (Sigma picryl sulfonic acid, Cat. No. P-2297) dissolved in water. After a 5 minute incubation at room temperature, the preparations were either passed over a PD-10 column to remove unreacted reagent or used as is the preparations were stored refrigerated and wrapped in foil to protect from light.

Human Liver Alkaline Phosphatase

The liver alkaline phosphatase (L-ALP) used in the following studies was human liver extract purchased from International Enzymes, Inc. The L-ALP was purchased in lyophilized form and was kept frozen. Prior to use, it was affinity purified by the procedure described above for B-ALP.

Example I

Production and Isolation of Monoclonal Antibodies B-ALP XI-4G6, B-ALP XI-10E3 and B-ALP XII-3B2

Balb/c mice were injected with either TNP-B-ALP or TNP-B-ALP with WGA.

(A) Tissue Culture

The murine myeloma fusion partner P3X63-AG8.653 (ATCC CRL 1580) and resulting hybridomas were maintained in culture in S-DMEM (Super Dulbecco's Modified Eagle Medium, with 10% NCTC-135 (Gibco 440–1100), 10% FBS, 1 mM oxaloacetic acid, 1 mM sodium pyruvate, 4 mM L-glutamine, 50 $\mu$g/ml gentamicin, and 10 $\mu$g/ml insulin). Cells were passaged regularly to maintain log phase growth. Early in the cloning procedures and in fusions, cells were grown in conditioned S-DMEM. A macrophage-myeloma cell line, P388D1 (ATCC TIB 63) was grown to confluency in S-DMEM. The supernatant was filtered and the conditioned media was used 1:10 in S-DMEM for cloning. Cells were eventually weaned from the conditioned media before freezing.

(B) Fusions

Fusions were done essentially according to the procedure of Milstein and Kohler, Nature 256:495–497 (1975). Spleens were aseptically removed from the mice and the fat and connective tissue trimmed from the spleens. The spleens were cut into small pieces and placed in a ground-glass tissue homogenizer. DMEM (7 ml) without FBS was added to the homogenizer and the plunger was pushed down several times to separate the cells. The suspension in the homogenizer containing the splenocytes was then added to $3.5 \times 10^7$ AG8.653 cells in 10–15 ml DMEM per spleen. The cells were centrifuged together at 800–1000 rpm for 5–7 minutes. The supernatant was discarded. Cells were fused by addition of 2 ml polyethylene glycol (50% in 75 mM Hepes, pH 8.01, "PEG") per spleen. PEG was added gently over three minutes followed by adding 1 ml per spleen DMEM gently over 1.5 minutes and 5 ml of S-DMEM per spleen over 2 minutes to dilute PEG.

The cell suspension was centrifuged at 800–1000 rpm for 5–6 minutes. Supernatant was poured off and the cells were slowly resuspended in 100–125 ml of HAT selection media (0.1 mM hypoxanthine and 0.4 mM aminopterin, 0.016 mM thymidine in S-DMEM) per spleen. The cell suspension was then plated out 175 $\mu$l per well in six to seven 96-well microculture plates. Cells were then incubated at 7% $CO_2$ and 37° C.

Cells were fed by removing 125 $\mu$l per well of spent media and adding 150 $\mu$l per well of HAT media between the fifth and seventh day after the fusion. A second feeding was done 2–3 days after the first feeding using the same procedure as the first time but using S-DMEM with only 0.1 mM hypoxanthine and 0.016 mM thymidine (HT media).

Fusions were screened when cell colonies were about 50% confluent, approximately 7–10 days after fusion and usually two days after the last feeding. The initial screening of clones was done in the enzyme linked immunosorbent assay ("ELISA") format. The ELISA protocol included coating microtiter plates with 20 μg/ml of rabbit anti-mouse antibodies. The blocking step was followed by incubation with the hybridoma supernatant fluids. The plates were incubated with B-ALP or L-ALP, followed by the addition of substrate to detect alkaline phosphatase activity.

(C) Cloning

Cells that were ELISA positive for the presence of specific antibodies were cloned by serial dilution.

The procedure was as follows. Contents from a well in a 96-well fusion plate were transferred to the top well of 2–6 columns in a 96-well tissue culture plate. Conditioned S-DMEM (150 μl), was pipetted into the other rows. Using a flow 12-channel pipetter, 50 μl were then transferred from the top row (containing the cells) down the plate, gently mixing by pipetting up and down several times in each row. Cells were recloned 3–4 times using this procedure to ensure single cell colonies.

(D) Freezing and Thawing

Cloned and stabilized cell lines that looked hopeful in preliminary screening were frozen and stored at −90° C. Prior to freezing, the cells were centrifuged at 800–1000 rpm for 5–7 minutes and then resuspended into freezing media (S-DMEM with 10% DMSO and 20% FBS). Freezing media was chilled in an ice bath before resuspending the cells. Once resuspended, the cells were immediately pipetted into one ml aliquots into Nunc Cryovials. Vials were placed in a styrofoam centrifuge tube tray, which provided insulation so that the cells would freeze gradually. The trays were left at −90° C. for at least 24 hours. The vials were then transferred to storage boxes at −90° C. or into nitrogen tanks within 48 hours.

Cells were thawed by warming the vials in a 37° C. waterbath to release the ice pellet. Cells were transferred and washed, to remove DMSO, into a 15 ml centrifuge tube containing 10 ml of cold S-DMEM and centrifuged at 800 rpm for 5–7 minutes. The supernatant was discarded and the cells were resuspended in 5–7 ml S-DMEM into one well of a six-well plate. Viability was checked after 24 hours.

(E) Screening

The hybridomas were initially screening by the general reverse ELISA screen. The clones were later screened by the competition ELISA to find clones that preferentially recognized B-ALP and not L-ALP. The clones were then screened in a radioimmunoassay ("RIA") using $^{125}$I-labeled B-ALP and competing with L-ALP or B-ALP.

Immunoenzyme Screen (1) 96-well microtiter plates were coated with 100 μl/well (2 μg/ml) of rabbit anti-mouse IgG, IgA, IgM heavy and light chains ("RAM"), diluted 1:100 in PBS.

(2) The RAM solution was dumped out and the plates blocked with 1% normal sheep serum ("NSS") (200 μl/well).

(3) The NSS solution was dumped out and 50 μl/well of the antibodies (in culture supernatant) was added and incubated at 37° C. for at least one hour.

(4) Plates were washed four times with a PBS buffer.

(5) B-ALP at 0.1 mg/ml in tris-buffered saline ("TBS") was added at 100 μl/well. The plates were incubated for one hour at 37° C.

(6) The plates were washed four times with a PBS buffer.

(7) Phosphatase substrate (Sigma, 104 Phosphatase Substrate tablets No. 104–105) was added to a buffer (0.246 mM MgCl$_2$, 9.7% v/v diethanolamine, pH 9.8) at 1 mg/ml until dissolved. Substrate was added to the plate at 100 μl/well and the plates placed on a shaker at room temperature until sufficient color developed (0.5–1.5 OD). The plates were read at 405 nm.

Screening Antibody Titer (1) and (2) were done as described above for the immunoenzyme screen.

(3) After the NSS solution was dumped out, 100 μl of PBS was pipetted into each well. An additional 100 μl was added to one row followed by 2 μl of serum. 100 μl was then transferred from each well in this row to the corresponding well in the next row (1:2 dilution) and this process was repeated from row to row. The 100 μl from the last row uptake was discarded. The plates were incubated for one hour at 37° C.

(4) through (7) were done as described above for the immunoenzyme screen. The serum antibody titer was defined as the dilution at which there is a 70% reduction from the highest point of the titration curve.

Subclassing ELISA (1) through (4) were done as described above for the immunoenzyme screen.

(5) Goat anti-mouse specific subclass antibodies conjugated to horseradish peroxidase were added to the plates. Each hybridoma antibody was tested (Fisher Biotech Clonotyping System No D5B100-HRPO) for light chain (lambda and kappa) and heavy chain (IgG1, IgG2a, IgG2b, IgG3, IgM and IgA). ABTS substrate (Sigma No. A-4798) in 0.1 M citrate, pH 4.2, plus 1:1000 of 30% stock solution of hydrogen peroxide, was added at 100 μl/well. After sufficient color developed, the plates were read at 414 nm.

(F) Ascites Production

Mice were primed with Incomplete Freund's Adjuvant (0.3 ml/mouse injected i.p.) to induce hybridoma growth. Two to four days after the injection, mice were injected with 3–5×10$^6$ hybridoma cells per mouse. The cells were centrifuged at 800–1000 rpm for 7 minutes and resuspended in 0.5 ml of Hanks Balance Salt Solution (Gibco 310–4025AG).

Generally the ascites antibody was ready for harvesting 7–10 days after the hybridoma cella were injected. The ascites fluid was tapped via an 18 gauge needle inserted into the abdomen of the mouse allowing the ascites fluid to drain through the needle into a tube. After each tap, the ascites fluid was allowed to clot at room temperature for 20–30 minutes. The ascites was centrifuged for 20–30 minutes at full speed in a Beckman TJ-6R centrifuge.

(G) Purification of Monoclonal Antibodies Purification by Protein A/G Columns

Affinica protein A/G prepacked columns from Schleicher and Schuell were used.

The column was equilibrated with 3 ml of binding buffer (1.5 M glycine, 3.0 M NaCl, pH 8.9). A 1:2 dilution of ascites or tissue culture medium, in binding buffer, were filtered through a 0.2μ filter and applied on the column at a rate of 0.5 ml/min. The column was washed with binding buffer until no absorbance at 280 nm was detected. Elution was performed with 0.2 M glycine-HCl, pH 2.5. Fractions of 1 ml were collected into tubes containing 1.0 M Tris-HCl, pH 9.0. Fractions with absorbance at 280 nm were pooled and dialyzed overnight against PBS.

Purification by Bakerbond ABx

A matrix of Bakerbond ABx beads was conditioned in 10 mM 2-(N-morpholino) ethane sulfonic acid ("MES") buffer, pH 5.4. Antibody solution was diluted 1:4 in 10 mM MES buffer, pH 5.4. After about 1 hour at room temperature the beads were washed with the MES buffer. Elution was performed with 0.1 M NaCl, 0.1 M Tris, pH 7.4. Following elution, dialyzations were performed against PBS.

Example II

Competitive Radioimmunoassay (A) Radiolabeling B-ALP and L-ALP

50 μl PBS and 1 mCi of [$^{125}$I] iodine were added to six PBS washed Iodo beads (Pierce) and incubated for 5 minutes at room temperature. 200 μl of pure enzyme (270 μg/ml) was added for an additional incubation of 30 minutes. The supernatant was then transferred to another tube and the beads were washed twice with 100 μl of PBS. The sample of 500 μl was then applied on a prewashed PD-10 column for the separation between bound and unbound [$^{125}$I] iodine.

(B) Radioimmunoassay

An RIA for the detection of B-ALP or L-ALP specific antibodies was performed by coating Costar flat bottom strips with 20 μg/ml of rabbit anti-mouse antibodies. After incubation overnight at 4° C., the strips were blocked with 1% NSS for 1 hour at 37° C. Following the washing step, monoclonal antibodies that were shown to react preferentially with B-ALP in the ELISA assay, were added for 1 hour at 37° C. After an additional washing step, 125I-labeled B-ALP with and without L-ALP, or with or without non-radioactive B-ALP was added. Radioactivity was measured using a Gamma counter.

When unlabeled B-ALP was used as the competing antigen, a concentration of 270 ng/ml was required for 50% tracer antigen displacement. In contrast, 100 μg/ml of the L-ALP antigen was required to displace 50% of the tracer antigen. This indicates that the antibodies were less than 1% cross-reactive with L-ALP as compared to B-ALP.

The following table summarizes the RIA results for several antibodies:

|  | RIA[1] % Inhibition of B-ALP*[2] | | |
| --- | --- | --- | --- |
| Antibody | w/L-ALP | w/B-ALP | Subclass |
| VIII-9C6[3] | 0 | — | IgG1 |
| XI-9D1[4] | 2 | 63 | IgM |
| XI-5F10[4] | 0 | 62 | IgG1 |
| XI-10C7[4] | 5 | 60 | IgM |
| XI-10E3[4] | 6 | 69 | IgG2b |
| XI-4G6[4] | 0 | 81 | IgG1 |
| XII-5D10[5] | 5 | — | IgG1 |
| XII-3B2[5] | 7 | 70 | IgG1 |
| SV-1H10[6] | — | — | IgG2b |

[1]mean value for n = 3
[2]B-ALP* is $^{125}$I-labeled B-ALP
[3]The immunogen was a combination of B-ALP and B-ALP with WGA
[4]TNP-B-ALP immunogen
[5]TNP-B-ALP with WGA immunogen
[6]Selective immune suppression. The mice received a primary boost of L-ALP (an undesirable cross-reactant), followed a couple of weeks later by a second boost of L-ALP. Then the next day, the mice received an immunization with GK1.5, a monoclonal antibody that inactivated T helper cells and induces tolerance. These mice then received several boosts with B-ALP before fusing.

FIG. 1 illustrates the epitope map of bone alkaline phosphatase, obtained by comparing the cross-reactivities of the monoclonal antibodies listed above. There are three epitopic sites recognized by the antibodies of this invention. Epitope I is recognized by monoclonal antibodies VIII-9C6, XI-9D1, XI-5F10, XI-10C7, XI-10E3, XII-5D10 and SV-1H10. Of particular importance is monoclonal antibody XI-10E3, which is produced by hybridoma cell line ATCC No. HB 11107. Epitope II is recognized by monoclonal antibody VIII-9C6 and XII-3B2. Of particular importance is monoclonal antibody XII-3B2, which is produced by hybridoma cell line ATCC No. HB 11108. Epitope III is recognized by monoclonal antibody XI-4G6, which is produced by hybridoma cell line ATCC No. HB 11106.

Example III

Sandwich ELISA with Buffer

The sandwich assay used one antibody to coat the plate ($Ab_1$), then added sample, then used a labeled second antibody ($Ab_2$) that was more specific for B-ALP. Biotin-avidin was chosen as the marker.

(A) Biotinylation of Anti-B-ALP Monoclonal Antibodies

Antibodies that showed very low cross-reactivity with L-ALP in the competitive RIA were used in the sandwich ELISA as labeled antibodies. Purified monoclonal antibodies at 1–12 mg/ml were dialyzed overnight against 0.1 M sodium bicarbonate, pH 8.2. A solution of the biotinylating reagent, Enzotin, was prepared in DMSO at the same concentration (mg/ml) as the antibody. Enzotin solution was added at 0.12 ml per ml of protein solution and mixed. The solution was incubated for 4 hours at room temperature or overnight at 4° C. Residual Enzotin was removed by dialysis against PBS-azide. The biotin-labeled antibodies were stored at 4° C.

(B) The Sandwich Assay

A sandwich ELISA was done to determine epitope specificity for the B-ALP monoclonal antibodies. ELISA plates were coated overnight at 4° C. with 100 μl/well of a 2 μg/ml solution of purified monoclonal antibodies in PBS. Plates were washed three times then blocked for about one hour with 200 μl/well of 3% bovine serum albumin-phosphate buffered saline ("BSA-PBS"). Plates were washed three times and each well was filled with 100 μl of 1% BSA-PBS/ 0.05% Tween-20. Next, 50 μl of a 6 μg/ml solution of B-ALP or 12 μg/ml of L-ALP was added to the wells in the top row and a three fold dilution series of the enzyme was made down the plate by serially transferring and mixing 50 μL of solution from the first row to the second, and so forth down the plate. Plates were incubated for one hour at 37° C. and washed. Individual biotin-conjugates of monoclonal antibodies were then added to each column of the plate at a concentration of 0.4 μg/ml. Plates were incubated for an hour, washed and then 100 μg/well of a 1:20,000 dilution of streptavidin-horseradish peroxidase ("HRP") was added to each well and incubated for 45 minutes at 37° C. Plates were washed and a solution of the substrate, 3,3',5,5'-tetramethylbenzidine ("TMB"), was added to each well. The reaction was stopped with 1 M $H_2SO_4$ and the absorbance was read at 405 nm.

Of the antibodies tested, results showed that XII-3B2 as $Ab_1$ and XI-4G6 as Ab2 were the best pair.

The following are characteristic of these antibodies:

(1) the monoclonal antibodies do not interfere with the catalytic properties of the B-ALP, since the monoclonal-bound enzyme is active; and (2) B-ALP recognition is unaffected by neuraminidase treatment for 15 minutes at room temperature. The monoclonal antibodies do not recognize the carbohydrate moieties.

Example IV

Sandwich ELISA with Serum

ELISA plates were coated overnight at 4° C. with 100 μl/well of a 2 μg/ml solution of the monoclonal antibody XII 3B2 in PBS. Plates were washed three times then blocked for about one hour with 200 μl/well of 3% BSA-PBS. Plates were washed three times and each well was filled with 100 μl of either 1% BSA-PBS/0.05% Tween-20, and 10% serum or purified B-ALP enzyme spiked into the buffer.

(A) Assay Specificity

The total "normal sera" tested was from about 300 males/females and of the 300 tested, calculations were performed for 80 "normal sera". "Normal sera" is defined as being from:
1. young, healthy volunteers
2. normal postmenopausal women, according to bone densitometry, biochemical markers available and physicians recommendations.

| Normal Sera, B-ALP data | |
|---|---|
| n | 80 |
| Average | 1.135* |
| Std. dev. | 0.211 |
| Std. error | .024 |
| Median | 1.1 |
| Minimum | 0.77 |
| Maximum | 1.78 |

*normalized: OD of sample/OD of standard serum

Plates were incubated for one hour at 37° C. and washed five times. XI-4G6 biotinylated monoclonal antibody was then added to each well at a concentration of 0.4 μg/ml in the same buffer. Plates were incubated for an hour, washed five times and then 100 μg/well of a 1:10,000 dilution of streptavidin-HRP was added to each well and the incubation continued for 45 minutes at 37° C. Plates were washed and a solution of TMB was added to each well. The reaction was stopped with 1 M $H_2SO_4$ and the absorbance was read at 405 nm.

The OD 405 readings, an indication for the B-ALP levels, were normalized against the reading of a standard serum that was always present in each of the ELISA performed. After the normalization of the OD 405 reading, the calculations were performed.

Standard curves were prepared using affinity purified B-ALP. The purified enzyme was spiked into buffer(1% BSA-PBS/0.05% Tween-20) or into 2 different normal sera (Z or A), as shown in FIG. 2. The B-ALP levels observed in serum sample were higher than those observed in buffer because each serum contains an endogenous level of B-ALP, which varies from sera to sera.

Ten sera samples from normal individuals were used for the determination of the correlation coefficient of the calculated versus spiked B-ALP concentrations in serum. Different enzyme concentrations were spiked into B-ALP depleted sera samples and the ELISA was performed in the presence of 1% Triton. The ELISA readings were compared with a standard curve that was obtained by spiking various amounts of B-ALP into buffer and determining the ELISA response (FIG. 3). The results depicted in FIG. 4 show good correlation (0.967) but lower assay response in serum than in buffer.

The cross-reactivity of the anti-B-ALP monoclonal antibodies with the liver isoenzyme of alkaline phosphatase ("L-ALP") was studied using several different techniques:

(1) The cross-reactivity of the anti-B-ALP monoclonal antibodies with L-ALP originated from the organ (liver) origin, is presented in Example II. It was shown to be less than 1%.

(2) The cross-reactivity to circulating L-ALP of anti-B-ALP monoclonal antibodies XII-3B2 and XI-4G6 in the sandwich ELISA was studied using purified L-ALP obtained from Dr. John F. O'Brien of the Mayo Clinic. The two purified isoenzymes were added at different concentrations. The results are summarized in FIG. 5 and the following table:

| Spiked [B-ALP] (ng/ml) | Spiked [L-ALP] (ng/ml) | Assay Response B-ALP OD 405 | Assay Response L-ALP OD 405 | Apparent [B-ALP] (ng/ml) | % cross-reactivity |
|---|---|---|---|---|---|
| 0.00 | | 0.052 | | | |
| 5.00 | | 0.079 | | | |
| 10.00 | | 0.090 | | | |
| 15.00 | | 0.108 | | | |
| | 500.00 | | 0.054 | 0.0 | 0.0 |
| | 750.00 | | 0.061 | 1.5 | 0.20 |
| | 1000.00 | | 0.082 | 7.5 | 0.75 |

The cross-reactivity of anti-B-ALP monoclonal antibodies with L-ALP from serum origin was found to be less than 1%.

(B) Comparison of Techniques for Detection of ALP in Serum

Three methods were compared:

(1) Measurement of total ALP activity in serum. The main contributors to the total ALP activity in serum are the bone and liver isoenzymes. Each one is responsible for about half of the total activity of ALP in normal serum.

(2) B-ALP and L-ALP can be quantified by the resolution of two component inactivation data obtained with a centrifugal analyzer as described by R. W. Forsmar and J. F. O'Brien in *Clin. Chem.* 37(3):347–350 (1991). Dr. O'Brien provided this data and the analysis consisted of three separate runs: total activity, phenylalanine inhibition and urea inactivation.

(3) The sandwich ELISA was performed using five sera from patents with Paget's disease (very high bone turnover) and five sera from patients with very high total ALP activity levels mainly due to the elevation in L-ALP isoenzyme. These latter patients were diagnosed as having cancer or AIDS.

Comparison of the ELISA using B-ALP specific monoclonal antibodies to the ALP assays currently available, revealed that the performance of the ELISA was excellent in detecting the bone isoenzyme. The data is presented in the following table:

| | PAGET'S SAMPLES | | | | |
|---|---|---|---|---|---|
| | Correlation Analysis | | | | |
| Test | N | Mean | Std. Dev. | Min. | Max. |
| Total ALP activity | 5 | 6.02 | 2.57 | 3.8 | 10.2 |
| B-ALP (ELISA) | 5 | 6.38 | 1.48 | 5.2 | 8.9 |
| Centrifugal analyzer | 5 | 7.12 | 3.04 | 4.7 | 12.2 |

Example V

Evaluation of the Efficacy of B-ALP as a Marker for Bone Formation

A sandwich ELISA was performed, similar to the procedure described above. ELISA plates were coated with 2 μg/ml of XII-3B2 monoclonal antibodies overnight at 4° C.

Following blocking with 3% BSA-PBS, 10% serum samples in 1% BSA-PBS/0.05% Tween-20, were applied for 1 hour at 37° C. Following a washing step, biotinylated XI-4G6 monoclonal antibody (0.4 µg/ml) was added for 1 hour, 37° C., and after another washing, streptavidin-HRP was added for 45 minutes, 37° C. TMB was the substrate and 1 M $H_2SO_4$ was used to stop the reaction. Absorbance was measured at 405 nm.

(A) Paget's Disease Study

Paget's disease is a chronic disease of the bone. Affected bones become thickened and their structure disorganized. Patients with Paget's disease have a very high bone turnover. Serum samples tested were from patients under medication in order to reduce the bone turnover. B-ALP levels were measured by the ELISA assay. The total alkaline phosphatase activity data was provided by Dr. Frederick Singer at Cedars-Sinai Medical Center. The observed elevation in the total ALP activity in Paget's patients is known to be mainly due to elevation in the B-ALP levels. The following table shows the expected correspondence between the B-ALP ELISA results and the total ALP results:

|      | Total ALP | B-ALP |
|------|-----------|-------|
| Min. | 1.03      | 1.30  |
| Mean | 3.83      | 4.40  |
| Max. | 10.2      | 8.9   |

In the table, the results are given as the ratio of the assay result to the average upper limit of the assay for normal samples. FIG. 6 summarizes the data from 17 patients with Paget's disease.

(B) Liver Patient Study

Fifteen serum samples from patients with liver disease were assayed for their B-ALP levels by a sandwich ELISA and the results compared to their total ALP levels (FIG. 7). The B-ALP levels detected in these patients had no correlation with the total ALP levels as would be expected if the assay is insensitive to L-ALP. Similar results were reported previously in Steinberg, et al., *Ann. Clin. Lab. Sci.* 21(5):305–314 (1991).

(C) Osteoporosis Study

Seven samples from untreated osteoporosis patients were checked for B-ALP levels using the ELISA. The results presented in FIG. 8 show that 5 out of 7 had elevated B-ALP levels.

(D) Hyperparathyroidism-Hypoparathyroidism Study

It is very important to monitor B-ALP levels in hyperparathyroidism and hypoparathyroidism. Patients with either of these diseases have normal levels of total ALP activity, but since bone turnover is definitely changed in these patients, being able to monitor these changes using a B-ALP assay can be very helpful for the physician. See Gonchoroff, *Clinica Chimica Acta* 199(1):43–50 (1991). The following table summarizes the B-ALP levels in serum from patients with hyperparathyroidism and hypoparathyroidism as determined by an ELISA:

|        | Normalized No.*                                    |
|--------|----------------------------------------------------|
| Hyper- | 1.28, 1.4, 1.59, 1.18, 1.46, 1.14, 0.91, 1.5, 1.14 |
| Hypo-  | 0.94, 0.46, 0.87, 0.64, 1, 0.97                    |

*Normalized = OD sample/OD standard serum

Example VI

Evaluation of a Sandwich Assay Format for B-ALP

The following assay format was evaluated for determination of B-ALP. A soluble immune complex, containing biotinylated anti-B-ALP:B-ALP and fluoresceinated anti-B-ALP, was captured on streptavidin coated plates and detected with an anti-fluorescein enzyme conjugate.

(A) Preparation of Fluoresceinated XII-3B2 and XI-4G6

(1) Preparation of 5-carboxyfluorescein oxybis(ethylamine)

(a) Activation of 5-carboxyfluorescein

Two hundred mg of 5-carboxyfluorescein (0.537 mmole) was dissolved in approximately 10 ml of dry N,N-dimethylformamide ("DMF"). To the solution was added 137.6 mg (0.668 mmole) N,N'-dicyclohexylcarbodiimide ("DCC") and 89 mg N-hydroxysuccinimide ("NHS") (0.778 mmole). The mixture was flushed with argon for a few minutes then sealed. After 3 hours, TLC was checked (10% MeOH in $CHCl_3$, plus 1% glacial acetic acid; $R_f$ for carboxyfluorescein, 0.40 and its NHS, 0.76) indicating incomplete reaction. An additional 50 mg of DCC was added and the reaction resumed for an additional 2 hours.

TLC was carried out again and completion of the reaction was indicated. The mixture was filtered to remove N,N'-dicyclohexylurea that was formed, yielding 5-carboxyfluorescein NHS ester.

(b) Coupling to oxybis(ethylamine)

2,2'-Oxybis(ethylamine) dihydrochloride (530 mg, 3 mmole) was dissolved in 6 ml of water, and the pH adjusted to 9.0 with triethylamine. The solution was then placed in an ice bath. 5-carboxyfluorescein NHS ester was added dropwise and the pH of the solution maintained between 8 and 9 with triethylamine. Approximately 30 ml of the Bio-Rad macroporous cation exchanger AG® MP-50 (20–50 mesh, $H^+$ form) was added and the mixture evaporated to dryness under reduced pressure. The resin was then washed thoroughly with water to remove the unreacted 5-carboxyfluorescein. The product and unreacted oxybis (ethylamine) was eluted subsequently with 10% $NH_4OH$. Repeated rotary evaporations with addition of water then methanol, removed the ammonium solution to dryness.

Further purification was carried out with Bio-beads SM-2 (20–50 mesh, 10 g). The above residue was first dissolved in methanol, the beads were added, followed by an equal volume of water. The content of the flask was then evaporated to dryness. The beads were washed with water extensively to remove the unwanted oxybis(ethylamine). The fluoresceinated amine compound was then eluted with methanol. Upon removal of the solvent, approximately 120 mg of product was obtained. By a different TLC solvent system (benzene:methanol:n-butanol:water, 1:1.5:2:1), it was found that a small amount of oxybis(ethylamine) remained. This was then subjected to preparative TLC and a single spot purity fluoresceinated oxybis(ethylamine) was obtained.

The fluoresceinated amine compound obtained was taken into methanol and purification via absorption to the Bio-beads was repeated. After washing with water (150 ml×3), the dye was then eluted again with methanol.

(2) Preparation of 5-carboxyfluorescein oxybis(ethylamido) 1-carboxycyclohexyl 4-methyl (N-maleimide) ("FOSMCC")

Twenty mg of the fluoresceinated amine (0.043 mmole) was dissolved in 3 ml of DMF and 15 mg of sulfo-succinimidyl 4-(N-maleimidomethyl) cyclohexane 1-carboxylate ("sulfo-SMCC") (0.034 mmole) was added. After three hours, the reaction was complete, as determined by TLC (benzene:methanol:n-butanol:water, 1:1.5:2:1, product $R_f$ 0.69). The product was isolated by preparative TLC. The product reacted completely with cysteine and gave a lower $R_f$ product ($R_f$ 0.42 in the above solvent system) on TLC.

(3) Preparation of S-acetylmercaptosuccinyl XII-3B2 and XI-4G6

To 2 mg of purified antibody in 1 ml of PBS was added 3.2 µl of S-acetylmercaptosuccinic anhydride ("SAMSA") solution (4.1 mg SAMSA in 27 µl of DMSO). After stirring on ice for 2 hours, the conjugate was dialyzed against 2 l PBS overnight ar 4° C.

(4) Cleavage of SAMSA-antibody with $NH_2OH$

To the SAMSA-antibody solution was added 0.11 ml freshly prepared $NH_2OH$ solution (65 mg $NH_2OH$ in 0.93 ml $H_2O$, argon). The reaction was allowed to proceed at room temperature for at least 1 hour under argon atmosphere.

(5) Conjugation of FOSMCC and SAMSA(SH)-antibody

After 1 hour incubation in the $NH_2OH$ solution, the material was passed on a G-50 column, which had been washed with 5 mM EDTA in PBS (argon). The fractions, with protein were pooled and divided in half. To each part, a different amount of FOSMCC solution (0.58 mg of FOSMCC and 100 µl of methanol:EDTA-PBS, 1:1) was added.

The reaction was allowed to continue overnight at 4° C. The conjugates were purified on a Sephadex G-50 column using PBS as the eluting solution. Fractions that contained the conjugate were pooled.

Determination of the fluorescein/protein ("F/P") ratio was as follows: one part by volume of 1 M disodium phosphate (monobasic), pH 8.92, was added to nine parts by volume of the conjugate solution. The pH of the final solution was 8.55. The optical density of the solution was scanned between 250 and 550 nm. The F/P ratio was then calculated using the following formula:

$$F/P = \frac{OD\ 495/80,000}{(OD\ 280 - OD\ 495 \times 0.146)/1.4/160,000}$$

(B) Biotinylation of XII-3B2 and XI-4G6

The biotinylation of XII-3B2 and XI-4G6 was done as described above in Example III.

(C) Immunoreactivity of Conjugated Antibodies

In order to make sure that the affinity of the monoclonal antibodies towards B-ALP did not change because of the conjugation, the following experiment was performed:

An ELISA plate was coated with 2 µg/ml of the different conjugates (biotinylated XII-3B2 and XI-4G6, and each one fluoresceinated with 1.5 F/P and 3 F/P) in PBS overnight at 4° C. Following blocking with 3% BSA-PBS, purified B-ALP was added for one hour at 37° C. and the activity of B-ALP was measured. All the conjugates were active in binding B-ALP.

(D) Preparation of Anti-fluorescein-HRP Conjugate (1) Preparation of Anti-fluorescein-SH One milliliter of 10.75 mg/ml anti-fluorescein antibodies ("anti-F") in 0.1 M sodium phosphate, 0.1 NaCl/pH 7.4 buffer at room temperature was mixed with 3.72 µl of 50 mg/ml S-acetylthioglycolic acid-NHS ester ("SATA") in DMF. The resultant mixture (Ab:SATA=1:12) was incubated at room temperature for one hour and then purified on a G-25 column (PD-10) equilibrated with 0.1 M sodium phosphate, 0.2 M NaCl, 5 mM EDTA/pH 7.0. The protected thiol groups were exposed by hydroxylaminolysis (calculated amount of 1 M hydroxylamine in 0.1 M sodium phosphate, 0.2 M NaCl, 5 mM EDTA/pH 7.0 and the pH was adjusted to 7.0 by addition of 10 M NaOH to the anti-F-SATA solution to get 0.1 M hydroxylamine concentration). The hydroxylamine treatment as performed at room temperature for one hour and then the mixture was purified on a G-25 column equilibrated with buffer (0.05 M sodium phosphate, 0.1 M NaCl, 5 mM EDTA $Na_2$/pH 6.0, which was degassed, then argon saturated) at 4° C. The protein-containing fractions were pooled; and after flashing with argon, the pool was covered and stored on ice until reaction with HRP-maleimide. Eight thiol groups were introduced per anti-F molecule.

(2) Preparation of HRP-maleimide

To 1.5 ml of 40 mg/ml HRP solution in 0.1 M sodium phosphate/pH 6.8 at 4° C., 10 mg of solid sulfo-SMCC was added and incubated at 4° C. for one and a half hours by stirring. The reaction mixture was then purified on a G-25 column equilibrated with buffer (0.05 M sodium phosphate, 0.1 M NaCl, 5 mM EDTA/pH 6.0) at 4° C. The HRP-containing fractions were collected and stored on ice until reacting with anti-F-SH. The number of maleimide groups per HRP molecule was determined to be 0.714.

(3) The Condensation Reaction

The condensation reaction was performed by adding the anti-F-SH solution into the HRP-maleimide solution to minimize the aggregation. To 3.5 ml of 12.2 mg/ml HRP-maleimide solution in buffer, was added 4.5 ml of 1.46 mg/ml anti-f-SH in buffer, while stirring at 4° C. (Ab:HRP= 1:26). The mixture was flashed with argon and then incubated at 4° C. for 2 hours in a capped vial.

(4) Blocking the Unreacted Maleimide and Thiol Groups

The unreacted maleimide groups were blocked first by adding 0.1 ml of 0.1 M 2-mercaptoethylamine in deionized water to get a concentration of 1.25 mM. After incubation for 30 minutes at 4° C., the remaining thiol groups were blocked by adding 0.1 ml of 0.378 M iodoacetamide in deionized water to get 3.8 mM iodoacetamide concentration. after incubating for 1 hour at 4° C., the reaction mixture was concentrated by Centriprep-30 Amicon concentrator and then purified on a PD-10 column in 0.05 M sodium phosphate/pH 7.4 to remove the small molecular weight materials before Sephacryl S-300 column chromatography.

The final conjugate mixture was purified on a Sephacryl S-300 column equilibrated with 0.05 M odium phosphate/pH 7.4 at 4° C. and 3.2 ml per fraction was collected. In the pooled conjugate peak, the number of HRP molecules conjugated per antibody molecule was determined to be anti-F:HRP=1:3.43. The conjugate was stored in 0.05 M sodium phosphate, 0.001% Thimerosal/pH 7.4 at 4° C. until use.

(E) Indirect Assay

20 µl of serum and 1.25 µg/ml of purified B-ALP, together with a mixture of 100 µl of 0.5 µg/ml of biotinylated XI-4G6 and fluoresceinated XII-3B2 were combined. Incubation was for 30 minutes at 37° C. 100 µl of 0.5 µg/ml of HRP labeled anti-fluorescein was added and incubated for an additional 30 minutes at 37° C. Then, 0.64 g of avidin coated glass beads were added for 30 minutes at 37° C. Four washings of the beads were done with PBS-0.1% Tween-20. TMB was added and the reaction stopped with 1 M $H_2SO_4$. This protocol had a low background and the binding of B-ALP was specific and dose-dependent, as is shown below:

| No | Human* Serum (µl) | B-ALP µg/200 µl | 4G6-biotin | 3B2-F | anti-F-HRP OD µl | 405 |
|---|---|---|---|---|---|---|
| 1 | 20 | 0 | + | + | 100 | 0.399 |
| 2 | 20 | 0.15 | + | + | 100 | 0.465 |
| 3 | 20 | 0.75 | + | + | 100 | 0.597 |
| 4 | 20 | 1.5 | + | + | 100 | 0.694 |
| 5 | 20 | — | — | + | 100 | 0.071 |

-continued

| Human* | B-ALP | | | anti-F-HRP | OD |
|---|---|---|---|---|---|
| No Serum (µl) | µg/200 µl | 4G6-biotin | 3B2-F | µl | 405 |
| 6 | 20 | — | + | — | 100 | 0.062 |
| 7 | 20 | — | — | + | 100 | 0.070 |
| 8 | 20 | — | — | — | 100 | 0.064 |

*The human serum added includes internal levels of B-ALP (F) Calibrations

A series of experiments were performed in order to determine the optimal antibody concentrations. The calibration was performed by keeping two antibody concentrations constant while changing the third one. Good assay results for an assay with indirect labeling can be obtained with:

XI-4G6-biotin: 20 ng/reaction
XII-3B2-Fluorescein: 100 ng/reaction
anti-F-HRP: 150 ng/reaction Calibrations were also done to determine a suitable concentration for an assay with direct labeling:

XII-3B2-HRP: 250 ng/reaction

Although the foregoing invention has been described in some detail by way of illustration and example for the purposes of clarity and understanding, it will be obvious that certain changes or modifications may be practiced within the scope of the appended claims.

What is claimed is:

1. A method for determining the presence of bone alkaline phosphatase in a sample suspected of containing said bone alkaline phosphatase, which comprises:
    (a) bringing together in an aqueous medium:
        (1) said sample,
        (2) a first antibody capable of specifically binding to a first epitopic site on said bone alkaline phosphatase,
        (3) a second antibody capable of specifically binding to a second epitopic site on said bone alkaline phosphatase,
        wherein said first and second epitopic sites are different and said first and second antibodies together form an immunocomplex with said bone alkaline phosphatase, if present, and wherein said first and second antibodies are selected from the group consisting of a monoclonal antibody produced by hybridoma cell line ATCC No. HB 11106, a monoclonal antibody produced by hybridoma cell line ATCC No. HB 11107, and a monoclonal antibody produced by hybridoma cell line ATCC No. HB 11108, with the proviso that said first and second antibodies are from different cell lines; and
    (b) examining said medium for the presence of said immunocomplex, the presence thereof being related to the presence of bone alkaline phosphatase in said medium.

2. The method of claim 1 where said first antibody is a monoclonal antibody produced by hybridoma cell line ATCC No. HB 11106 and said second antibody is a monoclonal antibody produced by hybridoma cell line ATCC No. HB 11107.

3. The method of claim 1 where said first antibody is a monoclonal antibody produced by hybridoma cell line ATCC No. HB 11106 and said second antibody is a monoclonal antibody produced by hybridoma cell line ATCC No. HB 11108.

4. The method of claim 1 where said first antibody is a monoclonal antibody produced by hybridoma cell line ATCC No. HB 11107 and said second antibody is a monoclonal antibody produced by hybridoma cell line ATCC No. HB 11108.

5. The method of claim 1 wherein at least one of said antibodies is detectably labeled or capable of being detectably labeled.

6. The method of claim 5 wherein said antibody is bound to a first specific binding pair member and a second specific binding pair member is bound to a detectable label, wherein said second specific binding pair member is complementary to said first specific binding pair member.

7. The method of claim 1 wherein one of said antibodies is bound to a support or capable of being bound to a solid support.

8. The method of claim 7 wherein said antibody is bound to a first specific binding pair member and a second specific binding pair member is bound to a solid support, wherein said second specific binding pair member is complementary to said first specific binding pair member.

9. In a method for determining the presence of bone alkaline phosphatase in a sample suspected of containing said bone alkaline phosphatase, which comprises:
    (a) bringing together in an aqueous medium said sample, a first antibody and a second antibody whereby an immunocomplex is formed with said first and second antibodies and said bone alkaline phosphatase, if present; and
    (b) examining said medium for the presence of said immunocomplex, the presence thereof being related to the presence of bone alkaline phosphatase in said medium;
    wherein the improvement comprises selecting said first and second antibodies from the group consisting of a monoclonal antibody produced by hybridoma cell line ATCC No. HB 11106, a monoclonal antibody produced by hybridoma cell line ATCC No. HB 11107, and a monoclonal antibody produced by hybridoma cell line ATCC No. HB 11108, with the proviso that said first and second antibodies are from different cell lines.

10. A method for determining the presence of bone alkaline phosphatase in a sample suspected of containing said bone alkaline phosphatase, which comprises:
    (a) bringing together in an aqueous medium:
        (1) said sample,
        (2) a first monoclonal antibody produced by hybridoma cell line ATCC No. HB 11106,
        (3) a second monoclonal antibody produced by hybridoma cell line ATCC No. HB 11107, and
        (4) a third monoclonal antibody produced by hybridoma cell line ATCC No. HB 11108,
        wherein said first, second and third antibodies are different, and two of said antibodies together form an immunocomplex with said bone alkaline phosphatase, if present, where at least one of said antibodies is detectably labeled or capable of being detectably labeled and at least one of said antibodies is bound to a support or capable of being bound to a solid support; and
    (b) examining said medium for the presence of said immunocomplex, the presence thereof being related to the presence of bone alkaline phosphatase in said medium.

11. The method of claim 10 wherein one of said antibodies is detectably labeled or capable of being detectably labeled and two of said antibodies are bound to a support or capable of being bound to a solid support.

12. The method of claim 10 wherein two of said antibodies are detectably labeled or capable of being detectably labeled and one of said antibodies is bound to a support or capable of being bound to a solid support.

13. A kit for use in an assay method, comprising in a packaged combination in predetermined ratios for combination with a sample according to said assay method, (a) a first antibody selected from the group consisting of a monoclonal antibody produced by hybridoma cell line ATCC No. HB 11106, a monoclonal antibody produced by hybridoma cell line ATCC No. HB 11107, and a monoclonal antibody produced by hybridoma cell line ATCC No. HB 11108; and (b) a second antibody selected from the group consisting of a monoclonal antibody produced by hybridoma cell line ATCC No. HB 11106, a monoclonal antibody produced by hybridoma cell line ATCC No. HB 11107, and a monoclonal antibody produced by hybridoma cell line ATCC No. HB 11108, with the proviso that said first and second antibodies are from different cell lines.

14. A monoclonal antibody produced by hybridoma cell line ATCC No. HB 11106, which antibody binds to an epitopic site on bone alkaline phosphatase.

15. A monoclonal antibody produced by hybridoma cell line ATCC No. HB 11107, which antibody binds to an epitopic site on bone alkaline phosphatase.

16. A monoclonal antibody produced by hybridoma cell line ATCC No. HB 11108, which antibody binds to an epitopic site on bone alkaline phosphatase.

* * * * *